United States Patent
Mehra et al.

(10) Patent No.: US 6,185,459 B1
(45) Date of Patent: Feb. 6, 2001

(54) METHOD AND APPARATUS FOR PREVENTION OF ATRIAL TACHYARRHYTHMIAS

(75) Inventors: Rahul Mehra, Stillwater; Michael R. S. Hill, Minneapolis; Stephanie M. Fitts, St. Louis Park; Luc R. Mongeon, Minneapolis, all of MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/373,699

(22) Filed: Aug. 13, 1999

Related U.S. Application Data

(63) Continuation-in-part of application No. 09/135,331, filed on Aug. 17, 1998, now abandoned.

(51) Int. Cl.⁷ .................................................. A61N 1/362
(52) U.S. Cl. .............................................................. 607/14
(58) Field of Search .................................. 607/14, 9, 4, 5, 607/15, 13

(56) References Cited

U.S. PATENT DOCUMENTS

| | | |
|---|---|---|
| 3,937,226 | 2/1976 | Funke . |
| 4,088,140 | 5/1978 | Rockland et al. . |
| 4,354,497 | 10/1982 | Kahn . |
| 4,375,817 | 3/1983 | Engle et al. . |
| 4,403,614 | 9/1983 | Engle et al. . |
| 4,404,972 | 9/1983 | Gordon et al. . |
| 4,407,288 | 10/1983 | Langer et al. . |
| 4,830,006 | 5/1989 | Haluska et al. . |
| 4,928,688 | 5/1990 | Mower . |
| 4,941,471 | 7/1990 | Mehra . |
| 5,158,079 | 10/1992 | Adams et al. . |
| 5,243,978 | 9/1993 | Duffin, Jr. . |
| 5,267,560 | 12/1993 | Cohen . |
| 5,344,430 | 9/1994 | Berg et al. . |
| 5,379,776 | 1/1995 | Murphy et al. . |
| 5,403,356 | 4/1995 | Hill et al. . |
| 5,411,524 | 5/1995 | Rahul . |
| 5,540,727 | 7/1996 | Tockman et al. . |
| 5,545,185 | 8/1996 | Denker . |
| 5,545,186 | 8/1996 | Olson et al. . |
| 5,584,867 | 12/1996 | Limousin et al. . |
| 5,584,868 | 12/1996 | Salo et al. . |
| 5,683,429 | 11/1997 | Mehra . |
| 5,713,929 | 2/1998 | Hess et al. . |
| 5,720,768 | 2/1998 | Verboven-Nelissen . |
| 5,730,141 | 3/1998 | Fain et al. . |
| 5,755,736 | 5/1998 | Gillberg et al. . |
| 5,814,085 | 9/1998 | Hill . |
| 5,846,263 | 12/1998 | Peterson et al. . |

FOREIGN PATENT DOCUMENTS

| | | |
|---|---|---|
| 0554208 | 8/1993 | (EP) . |
| 0813889 | 6/1997 | (EP) . |

OTHER PUBLICATIONS

"Prevention of Atrial Tachyarrhythmias Related to Advanced Inter-atrial Block by Permanent Atrial Resynchronization", by Mabo, et al, published in *Pace,* vol. 14, Apr. 1991, Part II, p. 648.

*Primary Examiner*—Scott M. Getzow
(74) *Attorney, Agent, or Firm*—Reed A. Duthler; Harold R. Patton; Girma Wolde-Michael

(57) ABSTRACT

A cardiac pacemaker and a method of its use. The pacemaker paces a patient's heart in a tachyarrhythmia prevention pacing mode for an extended time period, defines a metric of success of the tachyarrhythmia prevention pacing mode, monitors the metric over the extended time period and, responsive to the monitored metric, adjusts the tachyarrhythmia prevention pacing mode. Adjustment of the tachyarrhythmia prevention pacing mode may take the form of pacing the patient's heart with a different set of electrodes, pacing the patient's heart with a different tachyarrhythmia prevention pacing mode and/or terminating operation of the tachyarrhythmia prevention pacing mode.

31 Claims, 14 Drawing Sheets

METHOD AND APPARATUS FOR PREVENTION OF ATRIAL TACHYARRHYTHMIAS

This application is a CIP of Ser. No. 09/135,331, filed Aug. 17, 1998, now abandoned.

BACKGROUND OF THE INVENTION

The present invention relates generally to the field of implantable stimulators and more particularly to cardiac pacemakers and implantable anti-arrhythmia devices.

It has been proposed to reduce the incidence of tachyarrhythmias in the ventricle by using multiple site pacing. For example, in U.S. Pat. No. 3,937,226, issued to Funke, multiple electrodes are provided for location around the ventricles. In response to a sensed depolarization following a refractory period, at any of the electrodes, all electrodes are paced. All electrodes are similarly paced in the absence of sensed depolarizations for a period of 1000 ms. U.S. Pat. No. 4,088,140 issued to Rockland et al discloses a similar device, in which a pacing pulse is delivered only to a single electrode in response to a failure to sense during a 1000 ms period, and delivery of pacing pulses to multiple electrodes is triggered in response to sensed depolarizations occurring between 150 and 500 ms following delivery of a previous sensed depolarization or pacing pulse. U.S. Pat. No. 4,354,497, issued to Kahn adds sensing electrodes adjacent the septum of the heart and delivers pacing pulses to multiple electrodes spaced around the ventricles in response to sensed depolarizations at the ventricular electrodes which are not preceded by depolarizations sensed at the septum electrodes. Multi-site pacing in the ventricles has also been proposed to improve hemodynamic function, as in U.S. Pat. No. 4,928,688, issued to Mower. The Funke, Kahn, Rockland and Mower patents are all hereby incorporated herein by reference in their entireties.

Multi-site atrial pacing has also been proposed as a mechanism for reducing the incidence of atrial tachyarrhythmias. For example, multi-site pacing for arrhythmia prevention is discussed in U.S. Pat. No. 5,584,867, issued to Limousin et at, U.S. Pat. No. 5,683,429 issued to Mehra and U.S. Pat. No. 5,403,356, issued to Hill et al. and in the article "Prevention of Atrial Tachyarrhythmias Related to Advanced Inter-atrial Block by Permanent Atrial Resynchronization", by Mabo, et al, published in *Pace*, Vol. 14, April 1991, Part II, p 648. The Limousin, Mehra and Hill et al. patents are hereby incorporated herein by reference in their entireties.

Pacing methodologies employing only a single pacing site have also been proposed for prevention of tachyarrhythmias. For example, U.S. Pat. No. 4,941,471 issued to Mehra discloses a single site rate stabilization pacing method for use in the ventricles. An improvement to this pacing methodology is disclosed in U.S. Pat. No. 5,545,185 issued to Denker et al, and further improvements are disclosed in U.S. Pat. No. 5,814,085 issued to Hill, and U.S. patent application Ser. No. 08/764,568, filed on Dec. 16, 1996 by Peterson et al. An additional atrial overdrive arrhythmia prevention pacing mode which is disclosed in U.S. Pat. No. 5,713,929, issued to Hess et al. The Mehra, Hill, Hess et al. and Denker patents, as well as the Peterson et al. application are all hereby incorporated herein by reference in their entireties.

SUMMARY OF THE INVENTION

The present invention is directed toward preventing the occurrence of atrial or ventricular tachyarrhythmias by means of a pacemaker having the capability of delivering tachyarrhythmia prevention pacing therapies at single or at multiple locations within the atria and/or ventricles. The present invention accomplishes this desired goal by means of control and timing circuits and methods of operation which provide for optimization of the delivered pacing therapy by choosing which therapy, which electrodes and which pacing sites are employed, from among those available for tachyarrhythmia prevention pacing. The timing and control circuitry includes means for tracking the occurrences of tachyarrhythmias over defined extended time periods, such as days, weeks or months.

Pacing at multiple sites may be accomplished by delivering pacing pulses through separate electrode pairs, each pair located adjacent a different site within the atria or within the ventricles, may be accomplished by delivering pacing pulses between electrodes located adjacent different sites within the atria or within the ventricles or may be accomplished by delivering pulses between individual electrodes in the atria or ventricles and remote indifferent electrodes. The device may employ single or multi-site pacing in the atria, the ventricles, or in both the atria and the ventricles, with separate prioritized lists of therapies and/or electrodes and polarities programmed for the atria and the ventricles and may employ separate counts or durations of occurrences of tachyarrhythmia in the atria and the ventricles in order to induce switching of the electrode configurations used to pace the atria and the ventricles, independent of one another.

In some embodiments, in response to detection of a predetermined number of occurrences of tachyarrhythmias within a defined extended time period and/or detection of a predefined cumulative duration of tachyarrhythmias within the defined extended time period, the selection of pacing therapy and/or interconnection of the electrodes available for pacing is modified to disable a tachyarrhythmia prevention therapy and/or to change the tachyarrhythmia prevention therapy. With each subsequent detection of a defined number and/or cumulative duration of tachyarrhythmias within the a defined extended time period, the device may switch to another available therapy and/or set of electrodes and pacing sites until an effective tachyarrhythmia therapy is selected or until all available therapies have been determined to be ineffective.

For example, in a device embodied in the form of a multi-site atrial pacemaker having electrodes positioned to stimulate at two different locations within the atria, the device may initially employ first and second electrodes in contact with atrial tissue to stimulate at both locations using the pacing method disclosed in the above-cited Mehra et al '429 patent, and then, in response to detection of a defined number of occurrences and/or a defined cumulative duration of tachyarrhythmia within the defined extended time period, the pacemaker may employ the second electrode, in conjunction with an indifferent electrode to stimulate only the second location using the pacing method disclosed in the above-cited Mehra '471 patent.

In some preferred embodiments of the invention, upon detection of a defined number of occurrences of tachyarrhythmias and/or a defined cumulative total duration of tachyarrhythmias in the atria or the ventricles within a defined extended time period, the device checks to see if there is an available therapy and/or set of electrodes and polarities which offer the opportunity of reducing the frequency or duration of tachyarrhythmias. In these embodiments, a therapy and/or an associated set of electrodes and polarities not previously employed will, by definition, be considered as offering the possibility of reducing the frequency or duration of tachyarrhythmias. In addition, the device may record information with regard to the frequency and durations of occurrences of tachyarrhythmia in conjunction with a particular therapy and/or associated set of electrodes and polarities, and may consider any previously employed therapies and/or sets of electrodes and polarities as offering an opportunity for reducing the frequency or duration of tachyarrhythmias if the associated recorded information indicates reduced frequency or duration of tachyarrhythmias as compared to the electrodes and polarities currently being employed.

In other preferred embodiments of the invention the device automatically determines whether any tachyarrhythmia prevention therapy is desirable and, if so which therapy and/or set of electrodes and polarities will be initially employed, based upon the frequency and durations of occurrences of tachyarrhythmia in conjunction with the particular therapies and/or associated sets of electrodes and polarities available. In these embodiments the device may first determine whether tachyarrhythmias in the absence of tachyarrhythmia prevention therapies and/or multi-site pacing occur during a first extended time period with a frequency sufficient to warrant employment of a tachyarrhythmia prevention therapy. If so, the device thereafter may sequentially apply each of the available therapies and/or sets of electrodes and polarities for a second extended time period to determine which results in the lowest incidence of tachyarrhythmias. The device may select the therapy and/or set of electrodes and polarities associated with the lowest incidence of tachyarrhythmias, provided that the incidence of tachyarrhythmias is lower than with no tachyarrhythmia therapy delivered. In such devices, after initial selection of the most effective tachyarrhythmia prevention therapy and/or electrode sites and polarities, the device may continue to employ the selected settings for a third extended predetermined time period, for example a defined number of months, and on expiration of this extended time period repeat the process of determining whether a tachyarrhythmia prevention therapy is desirable and if so, which therapy is desirable.

In order to more closely tie the anti-arrhythmia therapies and/or electrodes and polarities employed by the device to the incidence of tachyarrhythmias, the device may focus on tachyarrhythmias which are initiated following delivery of a pacing pulse. For example, the device may check stored information on sensed and paced events to determine whether a pacing pulse initiated the short: inter-depolarization period which initiated the tachyarrhythmia, and apply the detected arrhythmia to the tachyarrhythmia count or cumulative tachyarrhythmia duration measurement only if the detected tachyarrhythmia is initiated following a pacing pulse.

In addition to or as an alternative to selection between different arrhythmia prevention pacing modes, a device according to the present invention may also operate to provide optimized parameters of a selected anti-arrhythmia pacing mode. For example, in the context of a rate stabilization pacing mode as described in the above cited Mehra and Denker patents, or in the context of an atrial overdrive pacing mode as described in the above cited Hess et al patent, the value of the increment added to the duration of a previously measured R-R interval to define the next escape interval maybe adjusted. In an analogous fashion, the delay time, if any, between pacing pulses delivered at multiple pacing sites or between sensed depolarizations at one pacing site and the delivery of a pacing pulse to a second pacing site may also be optimized as a function of the monitored result of the therapy provided.

In order to optimize the parameters of the anti-arrhythmia pacing therapy provided, the device monitors a specific metric associated with the success of the therapy in a manner analogous to that described above in conjunction with selection between arrhythmia prevention pacing modes. In this context, for example, frequency of occurrence of atrial or ventricular beats, occurrence of atrial or ventricular tachyarrhythmias, and the like may be monitored and compared to a desired defined endpoint condition, with operational parameters of the pacing mode presently in effect adjusted in an attempt to cause the measured metric to converge on the desired endpoint.

The desired endpoint may be defined as a range which may have only an upper bound, only a lower bound or both upper and lower bounds. More than one measured metric may be employed to determine success of the arrhythmia prevention pacing mode. A measured metric falling outside of a defined endpoint range may trigger a change in the pacing mode to more aggressive or less aggressive parameter settings. The time period over which the metric is monitored may extend for a few hours up to several weeks. For example, if the defined metric is frequency of atrial fibrillation, the defined metric range might be less than a physician programmed number occurrences of atrial fibrillation over a two day time period. In this case, the device would adjust the parameters of a provided antiarrhythmia mode, for example, adjust the increment provided in conjunction with the atrial overdrive pacing modality described in the above Hess patent, until the measured frequency of occurrences of atrial fibrillation per two day period was within the endpoint range. Alternatively, if the metric being measured is frequency of occurrence of PACs, the defined metric might be a defined range of PACs per hour, determined by the physician to represent an acceptable range of occurrences of PACs. In this embodiment, the aggressiveness of the atrial arrhythmia prevention pacing modality employed may be increased in response to the number of occurrences of PACs being in excess of the defined endpoint range, while the aggressiveness of the therapy might be decreased in response to an occurrence of less than the defined endpoint range of occurrences, in order to avoid over-treating the patient. In response to the number of PACs per hour falling within the defined range, the device would leave the parameter settings of the arrhythmia prevention pacing modality unchanged.

In some embodiments, the same monitored metric or metrics employed to optimize the parameters of an arrhythmia prevention pacing modality may also be employed to disable the arrhythmia prevention pacing modality in effect or to trigger the switch to an alternative pacing prevention modality, as substitute for or in addition to the various mechanisms described above for selecting arrhythmia prevention pacing modalities. For example, in response to adjustment of the arrhythmia prevention pacing modality to its most aggressive parameters (the parameters believed most likely to prevent occurrences of arrhythmias), in conjunction with a failure of the measured metric to fall within the defined variance from the desired endpoint for the measured metric, the device may disable the arrhythmia prevention pacing modality presently under way or trigger a switch to an alternative available arrhythmia prevention pacing modality.

DETAILED DESCRIPTION OF THE PREFERRED EMBODIMENTS

Figure 1:
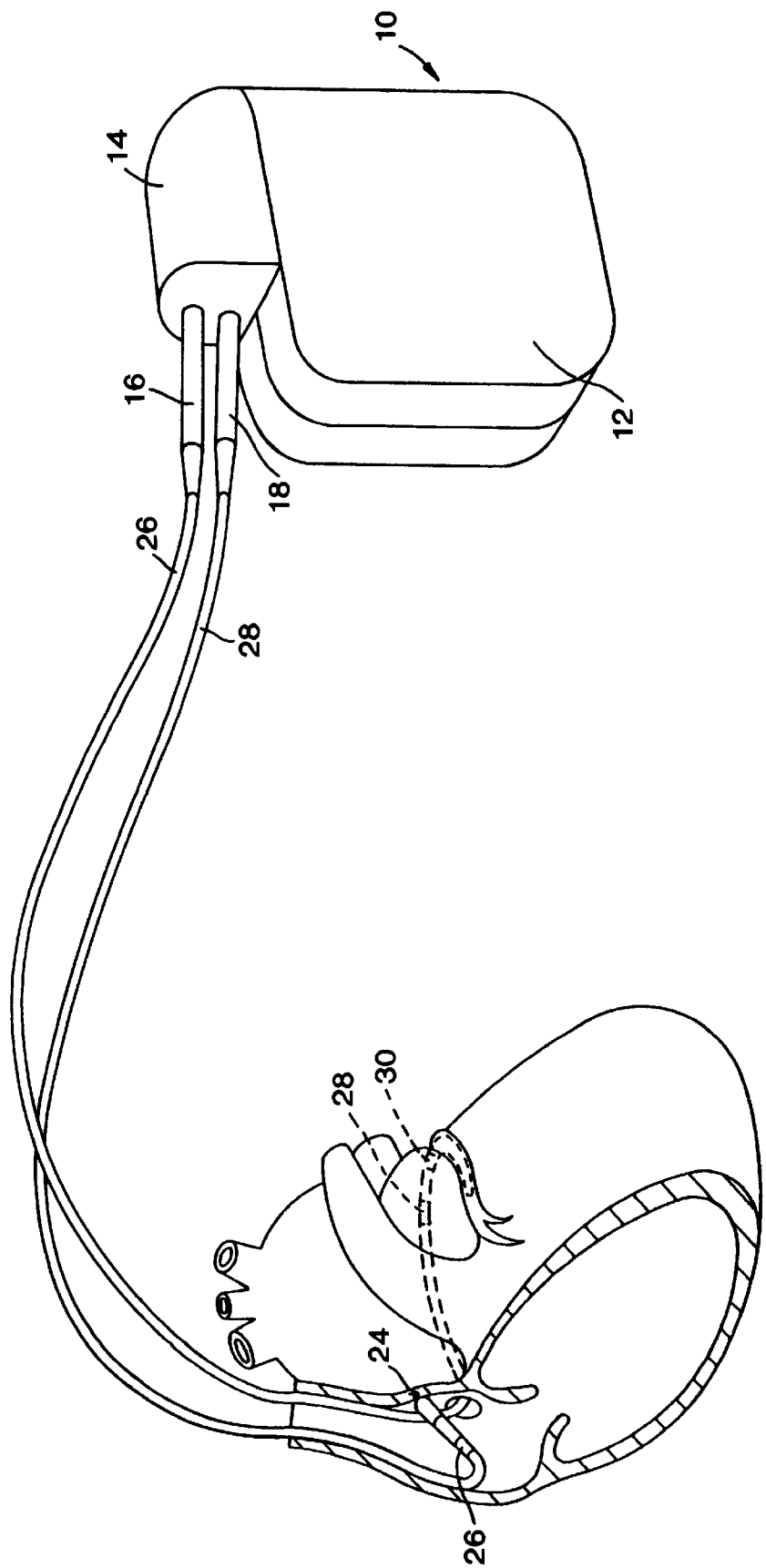
FIG. 1 is a drawing illustrating a multi-site atrial pacemaker according to the present invention.

FIG. 1 illustrates an implantable pacemaker 10 according to the present invention and an associated lead set. The pacemaker comprises a hermetically sealed enclosure 12 containing the pacemaker's circuitry and power source and carrying a connector block or header 14 into which the connector assemblies 18 and 16 of two pacing leads 20 and 22 have been inserted. Pacing lead 20 is a coronary sinus lead, and carries two electrodes 28 and 30 located thereon, adapted to be positioned adjacent the left atrium, within the coronary sinus/great vein of the patient's heart. Lead 22 is a right atrial pacing lead carrying a distal, screw-in electrode 24 and a proximal ring electrode 26.

In conjunction with practicing the present invention, the pacemaker may employ the electrodes on the various leads in a variety of combinations. Multi-site pacing may be accomplished by simultaneously delivering pacing pulses to the right atrium using electrodes 24 and 26, with electrode 24 serving as the pacing cathode and to the left atrium using electrodes 28 and 30, using either of electrodes 28 and 39 as the pacing cathode. Alternatively, multi-site pacing may be accomplished by delivering pacing pulses between electrodes 24 and 30 or between electrodes 24 and 28, with either of the two chosen electrodes serving as the cathode, in order to stimulate the right and left atria simultaneously by using electrode 24 and either of to electrodes 28 and 30 as pacing cathodes and a conductive portion of the enclosure 12 as a remote anode. Alternatively, the right atrium may be stimulated without stimulation of the left atrium by employing electrodes 24 and 26 or by employing electrode 24 in conjunction with a conductive portion of the housing of the device enclosure 12 to accomplish unipolar pacing. Similarly, pacing of the left atrium may be accomplished without corresponding pacing of the right atrium by pacing between electrodes 28 and 30 or by pacing between either of electrodes 28 and 30 and a conductive portion of the housing 12.

In conjunction with the present invention, it is preferable that the device 10 be configured to allow the physician to program a prioritized list of tachyarrhythmia prevention pacing therapies and/or pacing sites and electrode configurations therein, for sequential application by the device 10. For example, in the context of a device as illustrated in FIG. 1, the physician may request that the device 10 initially delivers pacing pulses to the right and left atria between electrodes 24 and 30 as part of a first arrhythmia prevention therapy, with electrode 24 being a cathodal electrode, delivers bipolar pacing pulses in the left atrium employing electrodes 28 and 30 as part of a second arrhythmia prevention therapy, with electrode 30 being a cathodal electrode, and delivers bipolar pacing in the right atria employing electrodes 24 and 26 as part of a third arrhythmia prevention therapy, with electrode 24 acting as a cathodal electrode. The first arrhythmia prevention therapy may, for example, simply be bi-atrial bradycardia pacing, while the second and third therapies may, for example, also include rate stabilization pacing as in the above-cited Mehra '471 patent.

The device in some embodiments may operate as follows. Following programming, the device employs electrodes 24 and 30 to simultaneously pace both the right and left atria. Over the course of a defined extended time period of weeks or months, the device detects a defined number and/or cumulative duration of tachyarrhythmias according to preset criteria. For example, a. tachyarrhythmia may be defined as a high atrial rate maintained for a minimum period of time. In response to the number and/or cumulative duration of detected tachyarrhythmia episodes equaling a preset value, the device preferably checks to see if there are any available electrode configurations which offer the opportunity of reducing the frequency of occurrence or the durations of atrial tachyarrhythmias. Because the next electrode configuration on the physician-defined list has not been tried, pacing the left atrium using electrodes 28 and 30 is then employed by the device. If the device detects the required number of occurrences and/or cumulative duration of tachyarrhythmias during a subsequent defined time period, the device will determine that the third electrode configuration, pacing the right atrium by means of electrodes 24 and 26, is untried, and will employ this electrode configuration. On detection of the required number of occurrences or cumulative duration of tachyarrhythmias, the device will then compare the number of tachyarrhythmias detected and the time period over which the tachyarrhythmias were detected for each of the three electrode configurations, and choose the electrode configuration associated with the lowest incidence of tachyarrhythmias. Operation of the device in this fashion continues, with the choice of electrode configuration altered automatically in response to an increase in the frequency of occurrence or cumulative duration of tachyarrhythmias using the previously selected electrode set, as compared to historical measurements of the frequency and/or duration of arrhythmias in conjunction with the other electrode combinations.

In an alternative set of embodiments, using the same prioritized list of arrhythmia prevention therapies, the device may operate for a, first period in the absence of any particular arrhythmia prevention therapy and/or alternate electrode configuration. For example the device may operate as a conventional AAI, bradycardia pacemaker, pacing at a single site in the right atrium. The device operates in this fashion for a first defined period of time, for example extending over a period of days or weeks, and monitors the number of detected tachyarrhythmia episodes and/or the durations of detected atrial tachyarrhythmias. If the frequency or duration of detected atrial tachyarrhythmias detected during this time period is less than a first preset threshold, the device may determine that specialized arrhythmia prevention pacing therapies and/or multi-site pacing or a combination of the two are not required.

If, however, during the first defined time period, a number or total duration of atrial tachyarrhythmias exceeding the first threshold are detected, the device may activate the first available tachyarrhythmia prevention therapy and/or alternate electrode configuration for a second defined period of time, typically less than the first defined period, again monitoring the frequency and/or durations of detected atrial tachyarrhythmias, followed by sequentially activating the second and third tachyarrhythmia prevention therapies and/or electrode configurations for the second defined extended time period and determining the frequency and/or durations of atrial tachyarrhythmias. After delivering all available tachyarrhythmia prevention therapies and/or employing all available electrode configurations, the device may compare the relative frequencies and/or durations of atrial tachyarrhythmias to determine which therapy and/or electrode configuration results in the lowest incidence of tachyarrhythmias, and enabling that therapy and/or set of electrodes and polarities, providing that the therapy and/or electrode configuration provides a reduced incidence of tachyarrhythmias compared to conventional single site bradycardia pacing as measured during the first time period.

As an preferred alternative to employing each of the available tachyarrhythmia prevention therapies and/or alternative electrode configurations for defined time periods and comparing the frequencies or cumulative durations of tachyarrhythmias detected therein, the device may instead continue operation in each of the available therapies and/or alternative electrode configurations until the earliest of the expiration of the defined second time intervals or the meeting of a defined tachyarrhythmia duration and/or frequency threshold. The relative incidences or durations of tachyarrhythmias per unit time may then be compared to chose the most desirable therapy and/or electrode configuration. Using this method, the time required to check the various available therapies and/or electrode configurations may be substantially reduced. Similarly, the initial operation of the device without use of tachyarrhythmia prevention therapies and/or alternate electrode configurations may preferably continue until the earliest of the expiration of the defined first time interval or the meeting of a defined tachyarrhythmia duration and/or frequency threshold, to reduce the time required to determine whether tachyarrhythmia prevention therapies and/or alternate electrode configurations are desirable.

In a simplified version of this embodiment of the invention, the device may be provided with only a single tachyarrhythmia prevention pacing therapy and/or a single alternate electrode configuration. In this embodiment, the device merely compares the frequency and/or duration of tachyarrhythmias during application of the arrhythmia prevention therapy and/or alternate electrode configuration with the frequency and/or duration of tachyarrhythmia incidences in the absence of arrhythmia prevention therapy and/or alternate electrode configuration, enabling application of the therapy and/or alternate electrode configuration only if they result in a reduced incidence of tachyarrhythmias.

In the event that the operation of the device and the selection of an initial arrhythmia prevention therapy is provided as described above, the device may subsequently operate according to the methodology set forth in conjunction with the previously described embodiments of the invention, periodically changing the tachyarrhythmia prevention therapy and/or the associated set of electrodes and polarities in response to the increase in the levels of tachyarrhythmias, selecting an alternative therapy and/or set of electrodes and polarities which provide a lower incidence of tachyarrhythmias, if available. Alternatively, the device may define a third extended time period, significantly longer than the first and second extended time periods. On expiration of this third time period, the device may repeat the sequence of operations described above to again determine whether tachyarrhythmia prevention therapies and/or alternate electrode configurations are desirable and if so which should be employed.

Figure 2:
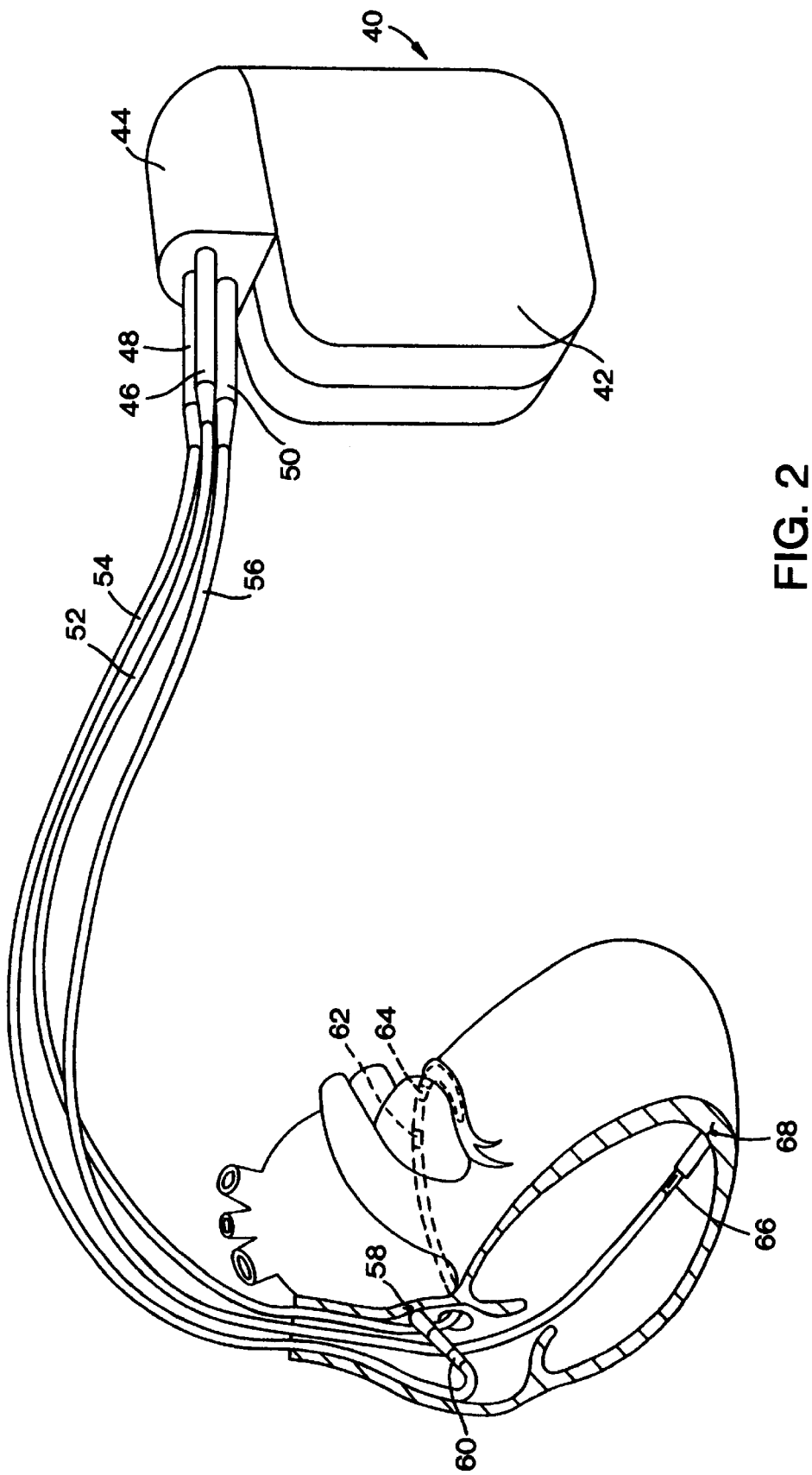
FIG. 2 is a drawing illustrating a multi-site atrial, single site ventricular pacemaker according to the present invention.

FIG. 2 illustrates an alternative embodiment of a pacemaker according to the present invention. Here the pacemaker 40 of FIG. 2 generally corresponds to the pacemaker 10 of FIG. 1, with the addition of ventricular pacing capabilities. The pacemaker comprises a sealed hermetic enclosure 42 containing the pacemaker's circuitry and power source and a connector block 44 which receives the connector assemblies 46, 48 and 50 of three pacing leads 52, 54 and 56. Leads 52 and 54 correspond to leads 20 and 22, respectively, of FIG. 1, and carry atrial pacing electrodes 58, 60, 62 and 64. Lead 56 is a ventricular pacing lead carrying a helical electrode 68 imbedded in the right ventricle of the heart and a, ring electrode 66. A device according to FIG. 2 may employ multi-site atrial pacing in conjunction with ventricular pacing, using pacing modalities such as DDD, DVI and DDI pacing.

Figure 3:
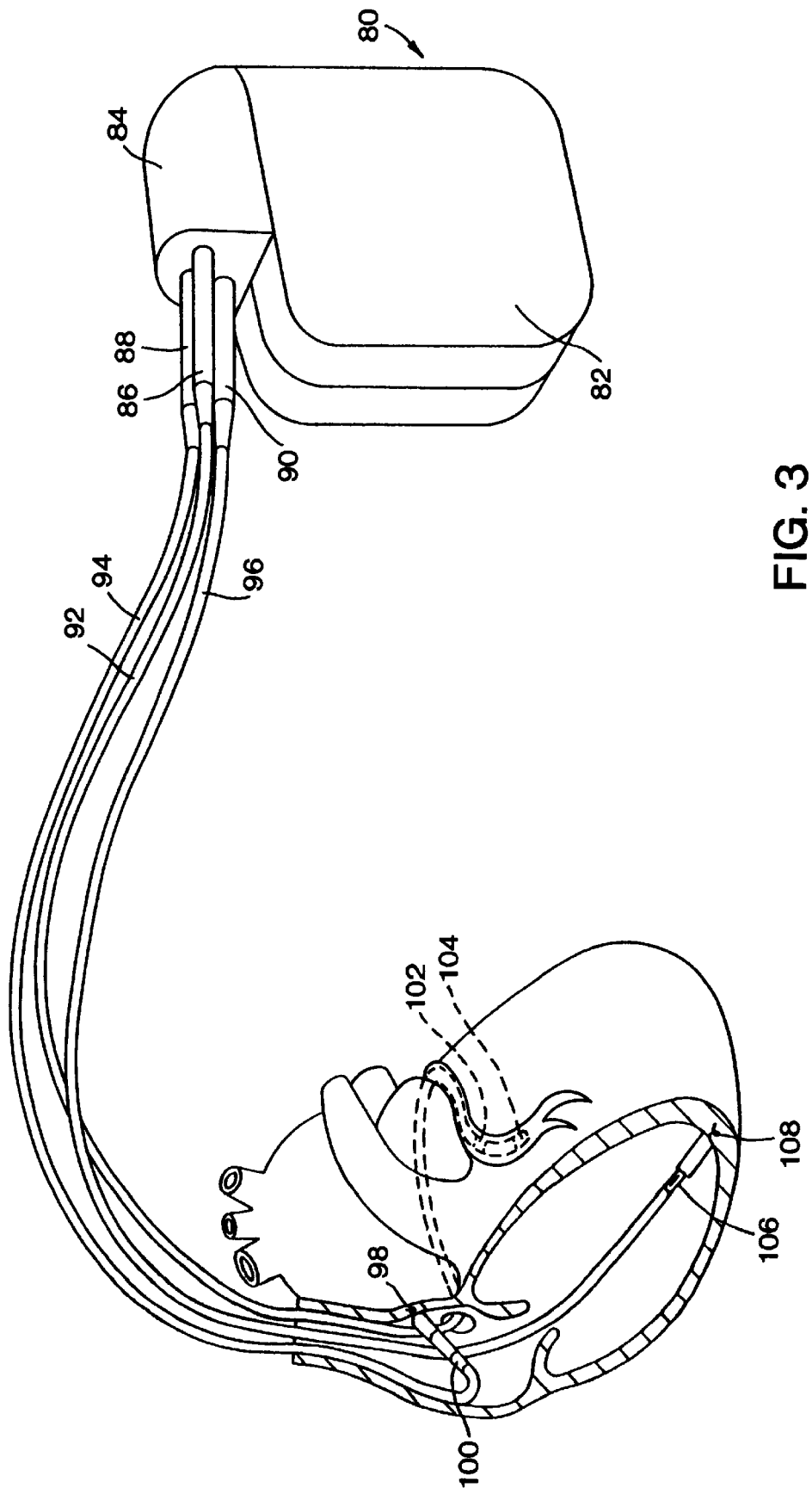
FIG. 3 is a drawing illustrating a single site atrial, multi-site ventricular pacemaker according to the present invention.

FIG. 3 is a second alternative embodiment of the pacemaker employing the present invention. In this embodiment of the present invention, pacemaker 80 corresponds generally to the pacemaker 40 in FIG. 2, including a hermetic enclosure 82 containing the pacemaker's circuitry and power source and a connector block 84 receiving the connector assemblies 86, 88 and 90 of leads 92, 94 and 96, respectively. In this embodiment, the pacemaker is configured to provide multi-site ventricular pacing in conjunction with atrial. sensing or pacing, so that multi-site ventricular pacing may be employed in conjunction with known pacing modes such as VDD, DDD, DVI and DDI. Leads 92, 94 and 96 correspond to leads 52, 54 and 56, respectively illustrated in FIG. 2, and carry pacing electrodes 98, 100, 102, 104, 106 and 108. In the case of lead 92, it has been advanced further into the coronary sinus/great vein than leads 20 and 52 of FIGS. 1 and 2, respectively, so that electrodes 102 and 104 are positioned adjacent the left ventricle of the heart. The set of leads provided in FIG. 3 thus gives the opportunity to provide multi-site pacing in the ventricles of the heart, by pacing the right ventricle using the electrodes 106 and 108 and pacing the left ventricle using the electrodes 102 and 104 or by pacing between electrodes 108 and either of the electrodes 102 and 104 or by pacing between electrode 98 and an uninsulated portion of the housing 82 and pacing between electrode 102 or 104 and an uninsulated portion of the housing 82. Pacing of the right ventricle alone without concurrent pacing of the left ventricle is possible using electrodes 106 and 108 or using electrode 108 in conjunction with an uninsulated portion of the housing 82. Similarly, delivering pacing pulses to the left ventricle only is possible using electrodes 102 and 104 together or by using either of electrodes 102 or 104 in conjunction with a conductive portion of housing 82. Operation of the device to select the desired pacing locations within the right and left ventricles and the desired electrode configuration may be accomplished in an analogous fashion to that described above in conjunction with FIG. 1 in the context of multi-site atrial pacing.

Figure 4:
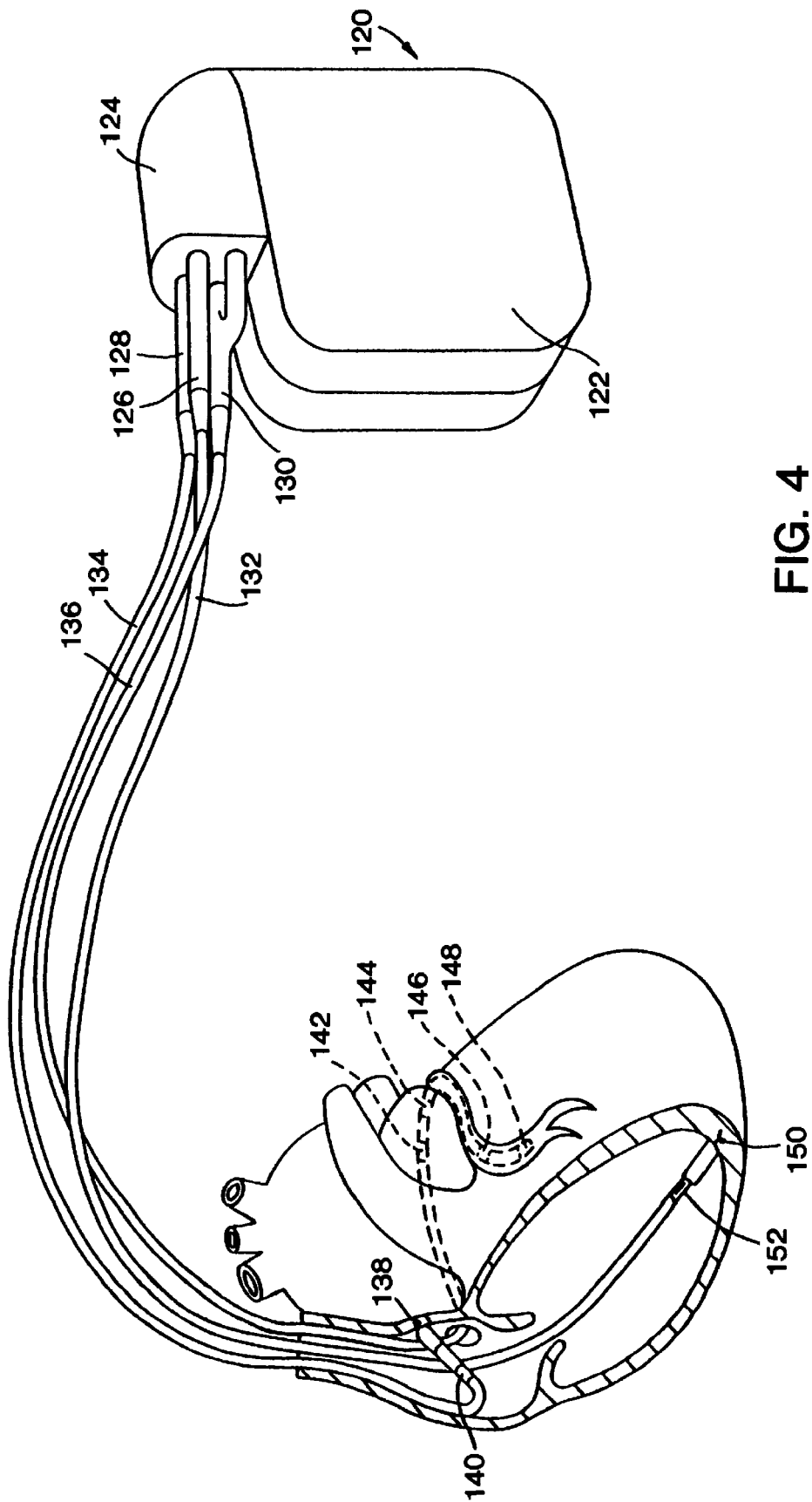
FIG. 4 is a drawing illustrating a multi-site atrial, multi-site ventricular pacemaker according to the present invention.

FIG. 4 illustrates an additional embodiment of a pacemaker according to the present invention. Pacemaker 120 corresponds generally to Pacemakers 10, 40 and 80 in FIGS. 1, 2 and 3, respectively, and includes a hermetic enclosure 122 containing the battery and circuitry of the pacemaker and a connector block 124 receiving the connector assemblies 126, 128 and 130 of pacing leads 132, 134 and 136. Pacing leads 132 and 134 correspond to pacing leads 90 and 92 of FIG. 3, and carry pacing electrodes 138, 140, 150 and 152. Lead 136 is provided with four electrodes 142, 144, 146 and 148, allowing pacing of the left atrium using electrodes 142 and 144 and pacing of the left ventricle using electrodes 146 and 148. In this embodiment of the invention, the device may select between pacing locations in the atria and the ventricle and may select among electrode configurations for accomplishing pacing in either or both of the atria and/or either or both of the ventricles in accordance with the basic mechanism described in conjunction with FIG. 1 for use in selecting electrodes to be used in atrial pacing.

Figure 5:
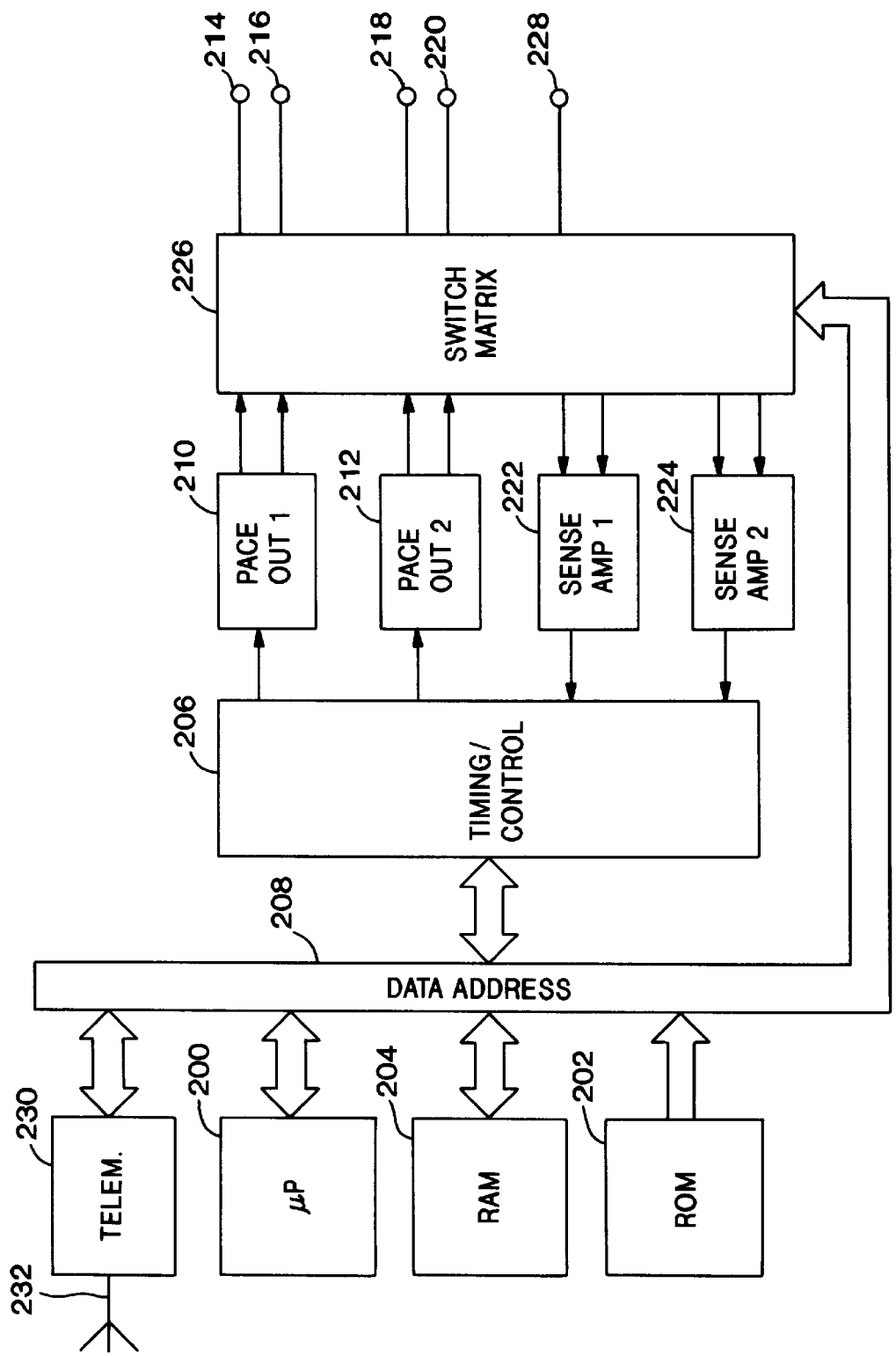
FIG. 5 is a block functional diagram of a first embodiment of a cardiac pacemaker appropriate for use in practicing the present invention.

FIG. 5 is a block diagram of a first embodiment of a pulse generator appropriate for use in conjunction with the present invention. The block diagram illustrated is particularly useful for pacemakers as illustrated in FIG. 1, directed towards multi-site pacing of the atria. Similarly, the device illustrated in FIG. 5 is also suitable for multi-site pacing of the ventricles, by themselves. The pacemaker includes a microprocessor 200 which controls operation of the device based on programming stored in read-only memory 202, communicated to the microprocessor 200 by means of data/address bus 208. The timing and control circuitry 206, under is microprocessors control, specifies the times of delivery of pacing pulses using the two pacing pulse amplifiers 210 and 212 and communicates occurrences of sensed events using sense amplifiers 222 and 224. Information with regard to the operation of the pacemaker including information as to the numbers and times of occurrences of tachyarrhythmias employed in the present invention is accomplished by means of random access memory 204.

Microprocessor 200 operates as an interrupt driven device, under software control, responsive to expiration of timers within timer/control circuitry 206 and in response to occurrence of sensed events, detected by sense amplifiers 222 and 224. Telemetry circuit 230 in conjunction with antenna 232 allow communication between the device and an external programmer, by means of which the physician can program a desired list of electrode configurations into memory 204. The general operational methodology of this device may correspond to any of the numerous available microprocessor controlled cardiac pacemakers, for example, as disclosed in U.S. Pat. No. 4,404,972 issued to Gordon et al., U.S. Pat. No. 4,830,006 issued to Haluska et al. or U.S. Pat. No. 4,407,288 issued to Langer et al., all incorporated herein by reference in their entireties. In particular, the operation of the device may generally correspond to that described in U.S. Pat. No. 5,411,524 issued to Mehra et al, also incorporated herein by reference in its entirety.

The device illustrated in FIG. 5 differs from the operation of the devices in the above described patent and in the above cited references disclosing multi-site pacing patents by means of a provision of a switch matrix 226 which operates under control of microprocessor 200 via data/address bus 208 according to the methodology of the present invention. Switch matrix 226 operates to interconnect the electrodes 214, 216, 218 and 220 with the pacing pulse generators 210 and 212 and with the sense amps 222 and 224 in any desired combination or configuration.

For example, electrodes 214 and 216 may correspond to electrodes 24 and 26 of FIG. 1, while electrodes 218 and 220 may correspond to electrodes 28 and 30 of FIG. 1. Electrode 228 may correspond to the housing of the device. In conjunction with operation of the device to simultaneously pace both atria, switch matrix 226 may couple pulse generator 210 with electrodes 214 and 216 and may couple pulse generator 212 with electrodes 218 and 220 to provide for pacing of both the right and left atria. Alternatively, pulse generator 210 might be coupled to electrodes 214 and 220, with the pacing pulse delivered therebetween in order to accomplish simultaneous pacing of both atria The device may similarly be employed to pace only one atrium using only electrodes 214 and 216 and either of the two output amplifiers 222 or 224 or to pace the other of the two atria using electrodes 218 and 220 and either of the pulse generators 210 and 220. Similarly, the device may be employed to pace either one or both of the ventricles of a patients heart, by locating electrodes 214 and 216 adjacent one ventricle and electrodes 218 and 220 adjacent the other ventricle.

Microprocessor 200, under control of programming stored in read only memory 302 also serves to implement the various tachyarrhythmia detection functions required by the device and to control the timing and delivery of pacing pulses in both conventional bradycardia pacing modalities and according to the physician's specified prioritized list of arrhythmia prevention pacing therapies. Arrhythmia detection mechanisms may correspond to any of those employed in prior art implantable anti-arrhythmia devices including anti-tachycardia pacemakers, implantable cardioverters and implantable defibrillators. Examples of arrhythmia detection methodologies appropriate for use in conjunction with the present invention include those described in U.S. Pat. No. 5,755,736 issued to Gillberg et al., U.S. Pat. No. 5,545,186 issued to Olson et al, U.S. Pat. No. 5,730,141 issued to Fain et al. and U.S. Pat. No. 5,379,776 issued to Murphy et al., all incorporated herein by reference in their entireties. It should be understood that any of the various known and available arrhythmia detection methodologies may be employed in conjunction with the present invention.

Arrhythmia prevention pacing therapies which may be implemented by microprocessor 200 and associated programming may, for example, correspond to those disclosed in U.S. Pat. No. 3,937,226 issued to Funke, U.S. Pat. No. 4,354,497 issued to Kahn, U.S. Pat. No. 5,683,429 issued to Mehra, U.S. Pat. No. 4,941,471 issued to Mehra, U.S. Pat. No. 5,545,185 issued to Denker, U.S. Pat. No. 5,713,929 issued to Hess et al., U.S. Pat. No. 5,158,079 issued to Adams et al. and U.S. Pat. No. 5,403,356 issued to Hill, some of which pacing modalities may also be delivered using multi-site pacing electrode systems, all of which are incorporated herein by reference in their entireties. The multi-site pacing therapies employed in conjunction with the present invention should also be understood to, include conventional bradycardia pacing therapies, delivered to multiple sites within the atria and/or ventricles, which are also sometimes valuable in preventing the occurrences of some tachyarrhythmias, as well as arrhythmia prevention pacing modalities as discussed above, delivered to multiple sites. Additional multi-site pacing therapies which may be employed include, for example, those described in U.S. Pat. No. 4,928,688 issued to Mower et al., U.S. Pat. No. 5,720, 768 issued to Verboven-Nelissen, U.S. Pat. No. 5,584,868 issued to Salo et al., U.S. Pat. No. 5,243,978 issued to Duffin and U.S. Pat. No. 5,267,560 issued to Cohen, all also incorporated herein by reference in their entireties.

Corresponding sets of arrhythmia detection methods and multi-site and arrhythmia prevention pacing methods should be understood to be defined by the microprocessors and associated programming provided in the pacemakers illustrated in FIGS. 6 and 7 below, constrained to the extent necessary by the available number of input amplifiers and pulse generator output circuits included in the pacemakers.

Figure 6:
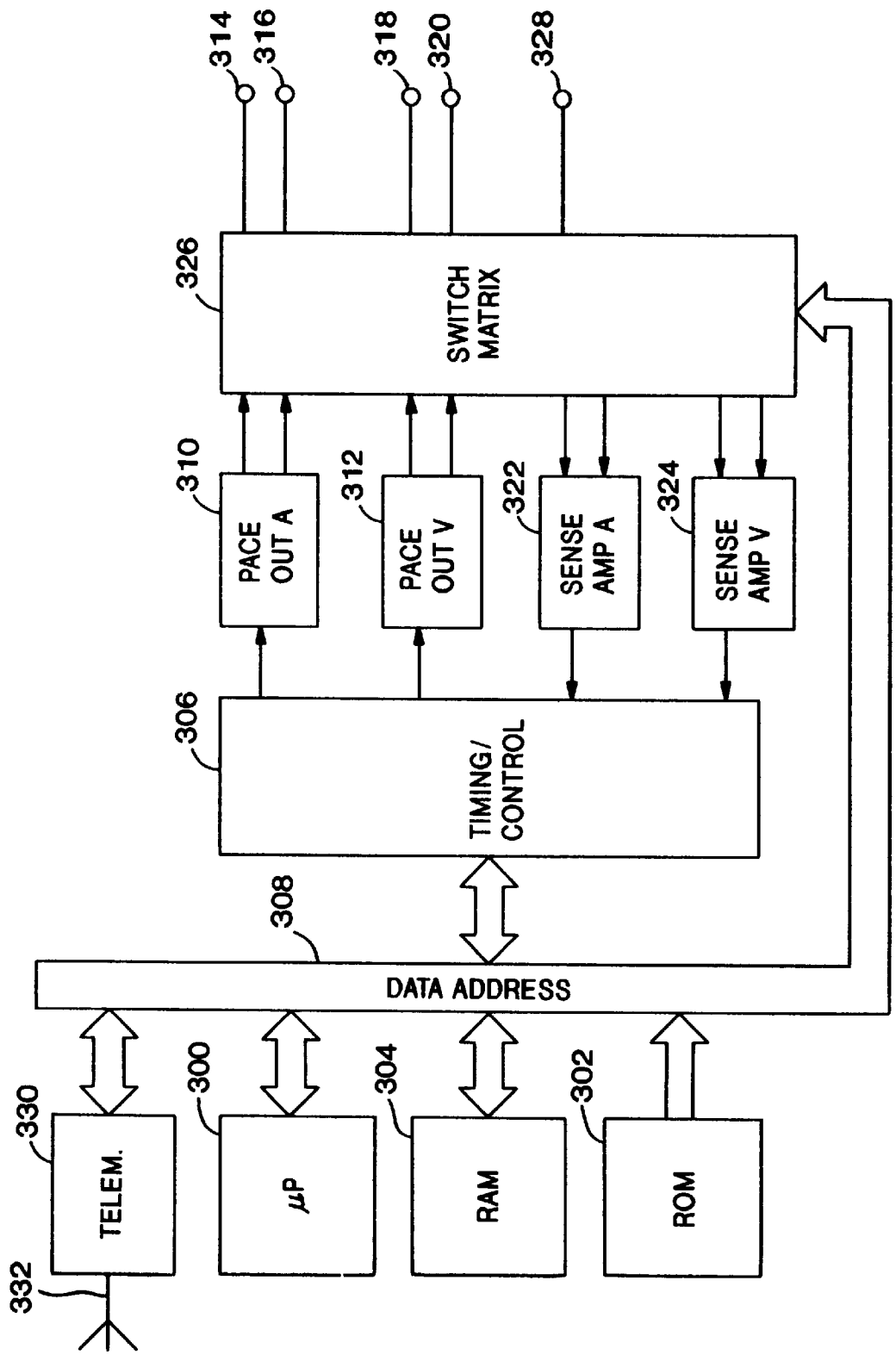
FIG. 6 is a block functional diagram of a second embodiment of a cardiac pacemaker appropriate for use in practicing the present invention.

FIG. 6 is an embodiment of a pacemaker which may be employed to provide multi-site atrial pacing in conjunction with ventricular pacing or multi-site ventricular pacing in conjunction with atrial pacing, corresponding to those illustrated in FIGS. 2 and 3. Microprocessor 300, ram 304, ROM 302, data/address bus 308, timing/control circuitry 306, output amplifiers 310 and 312 and input amplifiers 322 and 324, as well as switch matrix 326 all correspond generally to microprocessor 200, ram 204, ROM 202, data/address bus 208, timing/control 206, output amplifiers 210 and 212, input amplifiers 222 and 224 and switch matrix 226 of FIG. 5. Telemetry circuit 330 in conjunction with antenna 332 allows communication between the device and an external programmer, by means of which the physician can program a desired list of electrode configurations into memory 304. Operation of the device differs from that illustrated in FIG. 6 in that it is provided with programming stored in ROM 302 which allows microprocessor 300 to operate timing/control circuitry 302 to provide dual pacing modes such as DDD, DVI, VDD, DDI, and the like, using amplifier 310 to pace one or more of the atria, amplifier 312 to pace one or more of the ventricles, sense amplifier 322 to sense atrial depolarizations and sense amplifier 324 to sense ventricular depolarizations.

If multi-site atrial pacing is desired in conjunction with ventricular pacing, for example, electrode 314 may be placed adjacent the right atrium, electrode 316 may be placed adjacent the left atrium and electrodes 318 and 320 may be placed in the right ventricle. Electrode 328 may correspond to the housing of the device. Pacing of both atria may be accomplished by coupling atrial pacing amplifier 310 to pace between electrodes 314 and 316, while pacing of the right atrium individually maybe accomplished by coupling output amplifier 310 to electrodes 314 and 328 and pacing of the left atrium individually may be accomplished by coupling amplifier 310 to electrodes 310 and 328. Pacing of the ventricle maybe accomplished by coupling electrodes 318 and 320 to amplifier 312.

In the case in which multi-site ventricular pacing is desired in conjunction with atrial pacing, this may be accomplished by placing electrodes 314 and 316 in the right atrium, electrode 318 in the right ventricle and electrode 320 adjacent the left ventricle. Atrial pacing may be accomplished by coupling amplifier 310 to electrodes 314 and 316, while pacing of right and left ventricles simultaneously may be accomplished by coupling pulse generator 312 to electrodes 218 and 320 and pacing therebetween. Pacing of the right ventricle individually may be accomplished by coupling amplifier 312 to electrodes 318 and 328 while pacing the left ventricle individually may be accomplished by coupling amplifier 312 to electrodes 320 and 328. In the event that multi-site pacing is desired in both the atria and the ventricles, electrodes 314 may be located in the right and left atria respectively, and electrodes 318 and 320 located in the right and left ventricles respectively, and a switch matrix employed as described above to select pacing in either one or both of the atria or the ventricles.

Figure 7:
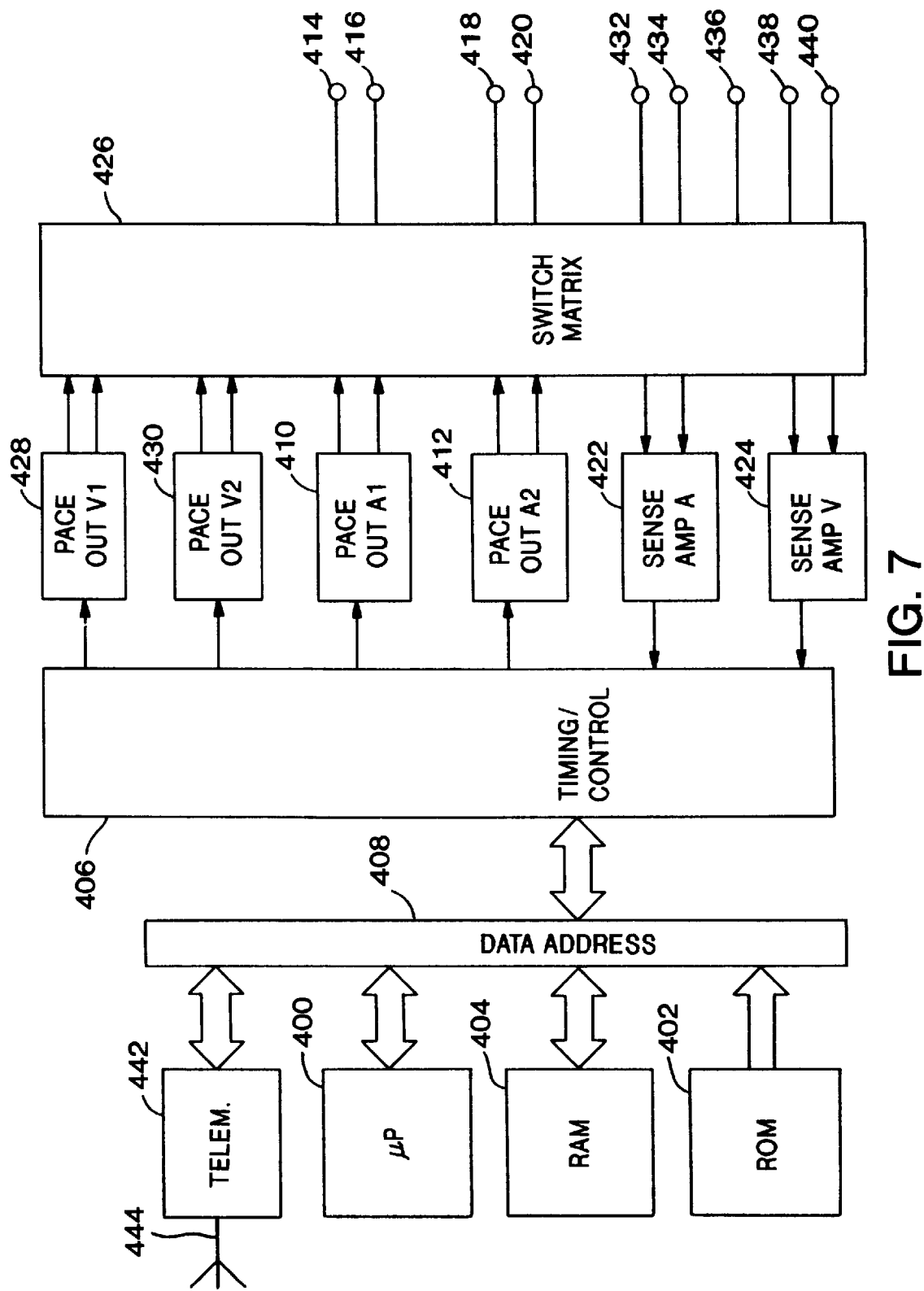
FIG. 7 is a block functional diagram of a third embodiment of a cardiac pacemaker appropriate for use in practicing the present invention.

FIG. 7 is a block diagram of a pacemaker which may accomplish any of the pacing modalities discussed above. Pacemaker in FIG. 7 corresponds generally to that in FIG. 5, with the exception that separate output amplifiers are provided for each of the right and left atria and each of the right and left ventricle, in conjunction with separate electrode pairs to be applied to each of the right and left atria and right and left ventricles. Microprocessor 400, Ram 404, ROM 402, data/address but 408, timing/control circuitry 406, pulse generators 410 and 412, sense amplifiers 422 and 424 and switch matrix 426 correspond generally to microprocessor 300, ram 304, ROM 302, data/address bus 308, timing/control circuitry 306, pulse generators 310 and 312, amplifiers 322 and 324 and switch matrix 326 of FIG. 6. Telemetry circuit 442 in conjunction with antenna 444 allows communication between the device and an external programmer, by means of which the physician can program a desired list of electrode configurations into memory 304. The device of FIG. 7 differs in the addition of two additional amplifiers 428 and 430 and the addition of additional electrodes 432, 434, 436 and 438 and by means of the correspondingly increased number of switches required for switch matrix 426 to allow interconnection of the four output amplifiers to the electrode pairs to allow for pacing of one or both of the ventricles or the atria. For example, electrodes 414 and 416 may be located in the right atrium, electrodes 418 and 420 located adjacent the left atrium, electrodes 432 and 434 may be located in the right ventricle, and electrodes 436 and 438 located adjacent the left ventricle, to provide a pacemaker corresponding to that illustrated in FIG. 4. Electrode 440 may correspond to the housing of the device. Pulse generators 420, 430, 410 and 412 may be selectively connected via switch matrix 426 to allow for pacing of one or both of the right and left atria and right and left ventricles, using either electrode pairs located adjacent each chamber or by pacing between electrodes, one located adjacent each chamber or by pacing between electrodes located adjacent each chamber and the enclosure of the device.

Figure 8:
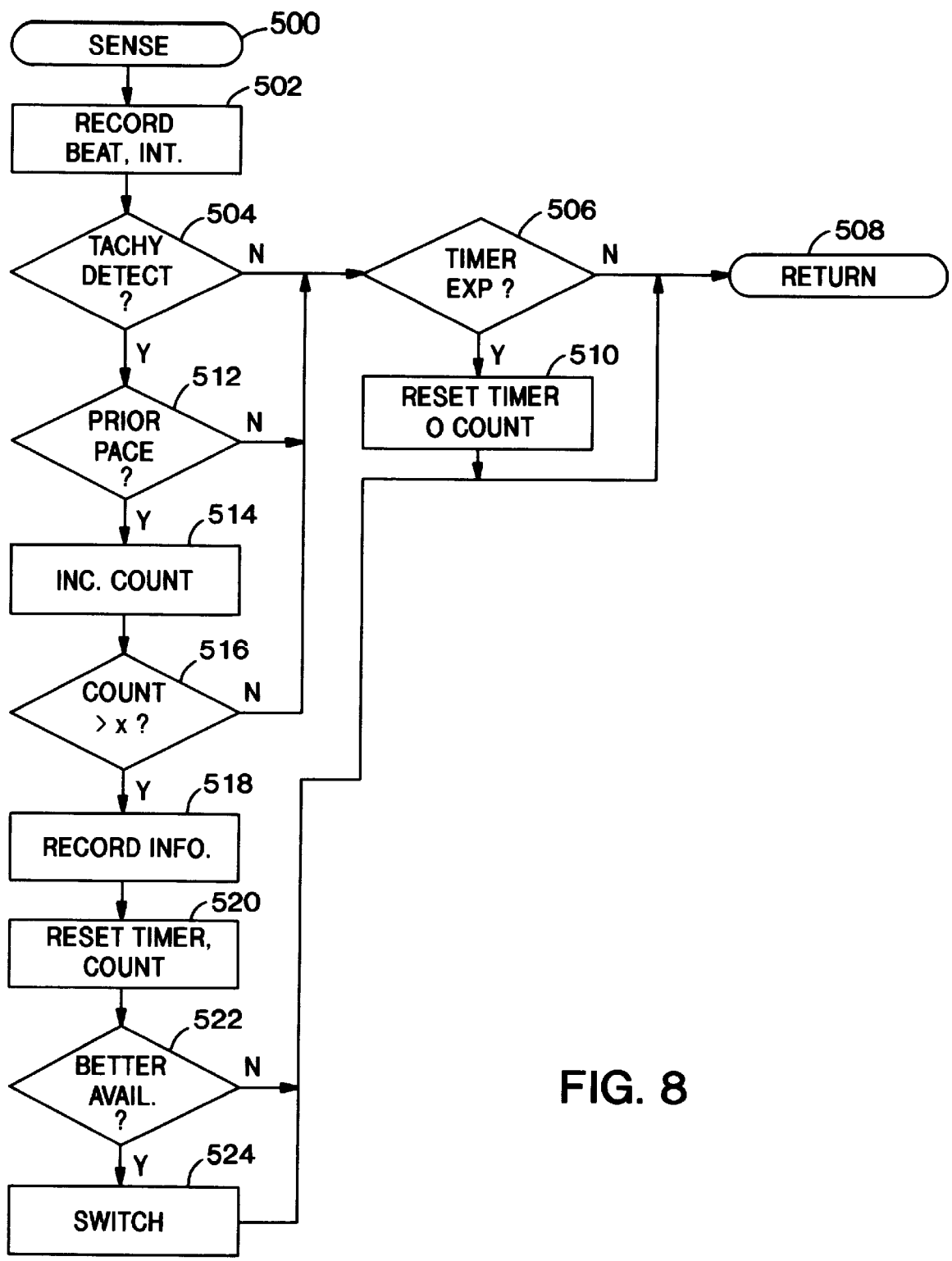
FIG. 8 is a functional flowchart, illustrating the basic operation of a pacemaker according to according to a first set of preferred embodiments of the invention.

FIG. 8 is a functional flow chart illustrating a first method of operation of a device according to a first embodiment of the present invention, which may correspond structurally to the devices of any of FIGS. 1–7. FIG. 8 illustrates a subset of the program stored within the memory of the device, controlling operation of the microprocessor, and reflects the operation of the device following sensing of an atrial or ventricular depolarization, depending upon the particular implementation of the invention. A device according to the present invention may employ the methodology illustrated in FIG. 8 following sensed atrial events if atrial pacing is available, following sensed ventricular events if ventricular pacing is available or following both atrial and ventricular events if atrial and ventricular pacing are both available.

In response to sensing of a depolarization at 500, the microprocessor records the type of depolarization sensed and the period separating the sensed depolarization from previous depolarizations of the same chamber and of other chambers, in order to that the stored information may be employed to determine whether a tachyarrhythmia is currently underway. The device checks at 504 to determine whether a tachyarrhythmia is underway. For example, the presence of a tachyarrhythmia may be confirmed by persistence of a rate in the chamber being sensed above a defined threshold, extending for at least a defined period of time. Alternatively, any other known tachycardia or tachyarrhythmia detection algorithm may be employed, including those set forth in the U.S. patents cited above.

In the event that tachyarrhythmia is not detected at 504, the device checks at 506 to determine whether the extended time period over which occurrences of tachyarrhythmia are monitored, as discussed above, has expired. The extended time period is preferably at least several days and more preferably at least several weeks. If the timer has expired, the timer is reset at 510 and the count of occurrences of tachyarrhythmias is correspondingly reset at 510 and the device returns at 508 to pacing the atria and/or ventricles using the electrode configuration previously selected.

In the event that tachyarrhythmia is detected at 504, the device may optionally check at 512 to determine whether the event which preceded the first short period of the detected tachyarrhythmia was a paced event in the chamber in which the tachyarrhythmia is detected. If so, a count of detected occurrences of tachyarrhythmia is incremented at 514. If not, the device checks to see if the extended time period is expired at 506, as discussed above. Alternatively, step 512 may be omitted, and the device may increment the count of occurrences of tachyarrhythmia each time the tachyarrhythmia is detected, irrespective of whether the tachyarrhythmia is preceded by a delivered pacing pulse in the chamber in which the tachyarrhythmia is detected. It is believed that inclusion of the step illustrated at 512 may be preferable in some patients, in that it tends to more accurately identify tachyarrhythmias which might have been initiated by delivery of cardiac pacing pulses.

At 516 the incremented count of tachyarrhythmia occurrences is checked against a preset threshold, and, if the count has not exceeded the preset threshold, the microprocessor checks at 506 to determine whether the extended time period has expired, and proceeds as described above. If, however, the count of detected tachyarrhythmias at 516 does exceed the defined threshold, the microprocessor records information at 518 with regard to the frequency of occurrence and/or duration of tachyarrhythmias, the present tachyarrhythmia prevention therapy and the present electrode configuration of the device. For example, the microprocessor may record in random access memory associated therewith, the therapy presently in effect, the particular electrodes employed to pace the chamber in which the tachyarrhythmia is detected, the polarities of the electrodes and the time span over which the required number of tachyarrhythmia occurrences was detected. As discussed above, this information may later be employed in order to determine whether the existing arrhythmia prevention therapy and/or electrode configuration. is performing better than other available therapies and/or electrode configurations.

The extended time period and the tachyarrhythmia count are reset at 520, and at 522 the microprocessor checks to determine whether a therapy and/or an electrode configuration is available which offers the opportunity of a reduced incidence of tachyarrhythmias. By definition, untried therapies and/or electrode configurations that are on the list of configurations programmed into the device by the physician are considered to offer the possibility of a reduced incidence of tachyarrhythmias. Alternatively, the previously attempted arrhythmia prevention therapies and/or electrode configurations which have, based on information recorded by the microprocessor, provided a lower incidence of tachyarrhythmias are also considered to offer the possibility of a reduced incidence of tachyarrhythmias. In the absence of untried therapies and electrode configurations, the therapy and/or electrode configuration having the lowest incidence of tachyarrhythmia per unit of time will be employed. At 524, the arrhythmia prevention therapy and/or electrode configuration and/or selected pacing sites are modified as appropriate, and the device continues to operate using its newly selected therapy and/or electrode configuration. If the historical information stored by the microprocessor with regard to other therapies and electrode configurations does not indicate the opportunity for a lower incidence of tachyarrhythmias, the device continues to operate at 508 using the present therapy and electrode configuration and continues to monitor occurrences of tachyarrhythmia. By the mechanism described above, as the arrhythmic substrate of the heart changes over time, the pacemaker automatically has the ability to optimize the tachyarrhythmia prevention therapy, the pacing site or sites employed by the pacemaker and/or the electrode configurations employed at the various pacing sites.

Figure 9:
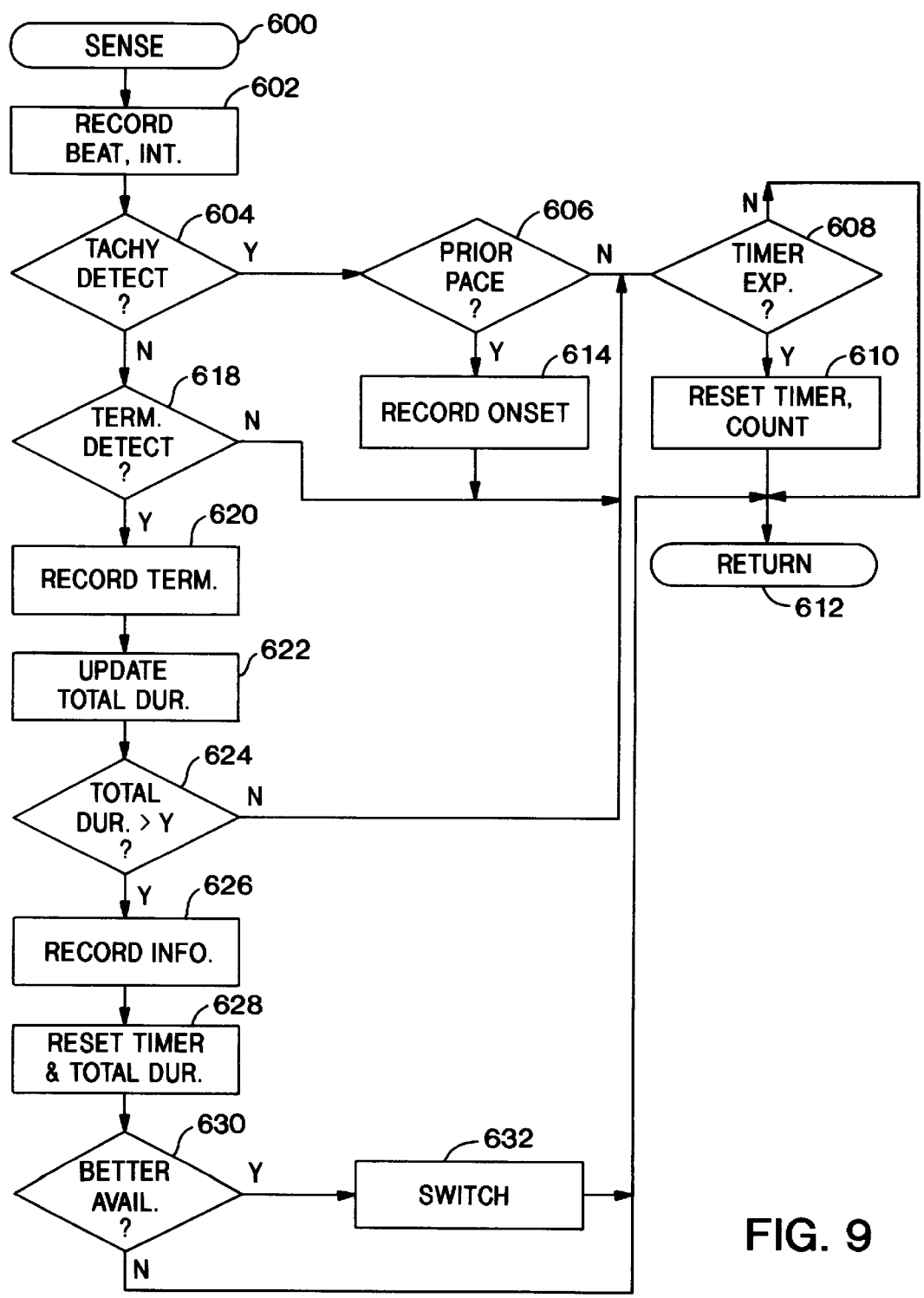
FIG. 9 is a functional flowchart, illustrating the basic operation of a pacemaker according to according to a second set of Preferred embodiments of the invention.

FIG. 9 is a functional flow chart illustrating an alternative method of operation of a pacemaker according to the present invention, which may correspond structurally to the devices of any of FIGS. 1–7. Like the method of operation illustrated in FIG. 8, this portion of the software stored in the read-only memory of the device is entered at 600 in response to a sensed atrial or ventricular depolarization, and the associated information concerning the depolarization is recorded at 602. At 604, the microprocessor checks to determine whether a tachyarrhythmia has been initiated. If so, the microprocessor optionally checks at 606 to determine whether the detected tachyarrhythmia was preceded by a paced beat, as discussed above in conjunction with FIG. 8. If so, the time of onset of the tachyarrhythmia is recorded at 614. As discussed above, the device may alternatively record the onset of a tachyarrhythmia regardless of whether it was preceded by a paced beat or not. In either case, the device then checks at 608 to determine whether the extended time period has expired at 608. If so, the device resets the extended time period and the total duration of tachyarrhythmia episodes at 610. In either case, the device then continues operation at 612 using the electrodes configuration previously employed.

In the event that tachyarrhythmia is not detected at 604, or in the event that tachyarrhythmia was previously detected at 604 and continues to be underway, the device checks at 618 to determine whether termination of the tachyarrhythmia has been detected. If not, the device checks at 608 to determine whether the extended time period has expired and continues as described above. If, on the other hand, termination of the tachyarrhythmia has been detected, the device records the termination at 620 and employs the difference between the time of onset and the time of termination to update a cumulative measurement of total duration of tachyarrhythmia episodes at 622.

At 624, the microprocessor compares the total duration of tachyarrhythmia episodes with a preset threshold value Y. If the total duration of tachyarrhythmia episodes accumulated does not exceed Y, the device returns to check to determine whether the extended time period has expired at 608 and continues as described above. If, however, the total duration of detected tachyarrhythmia episodes exceeds the preset threshold, information regarding the anti-arrhythmia pacing therapies and/or electrode configuration presently in effect in conjunction with information concerning the detected tachyarrhythmias is recorded at 626, including the amount of time required in order to detect the specified total cumulative duration of tachyarrhythmia episodes. This information is used as described above in comparing the therapy and/or electrode configuration presently in effect to other available therapies and/or electrode configurations. The extended time period and the measurement of total duration of tachyarrhythmia episodes is reset at 628, and the device checks as discussed above, to determine whether a therapy and/or electrode configuration offering the opportunity for reduced frequency of tachyarrhythmias is available. If so, the pacemaker select the new therapy and/or electrode configuration at 632, and the device continues operation at 612 using the newly selected therapy and/or electrode configuration. If, based on the historical information recorded by the microprocessor, the other available therapies and/or electrode configurations do not appear to offer the likelihood of a reduction in the overall duration of tachyarrhythmia, the device returns-to its previous operation using the arrhythmia prevention therapy and electrode configuration presently in effect at 612.

Figure 10:
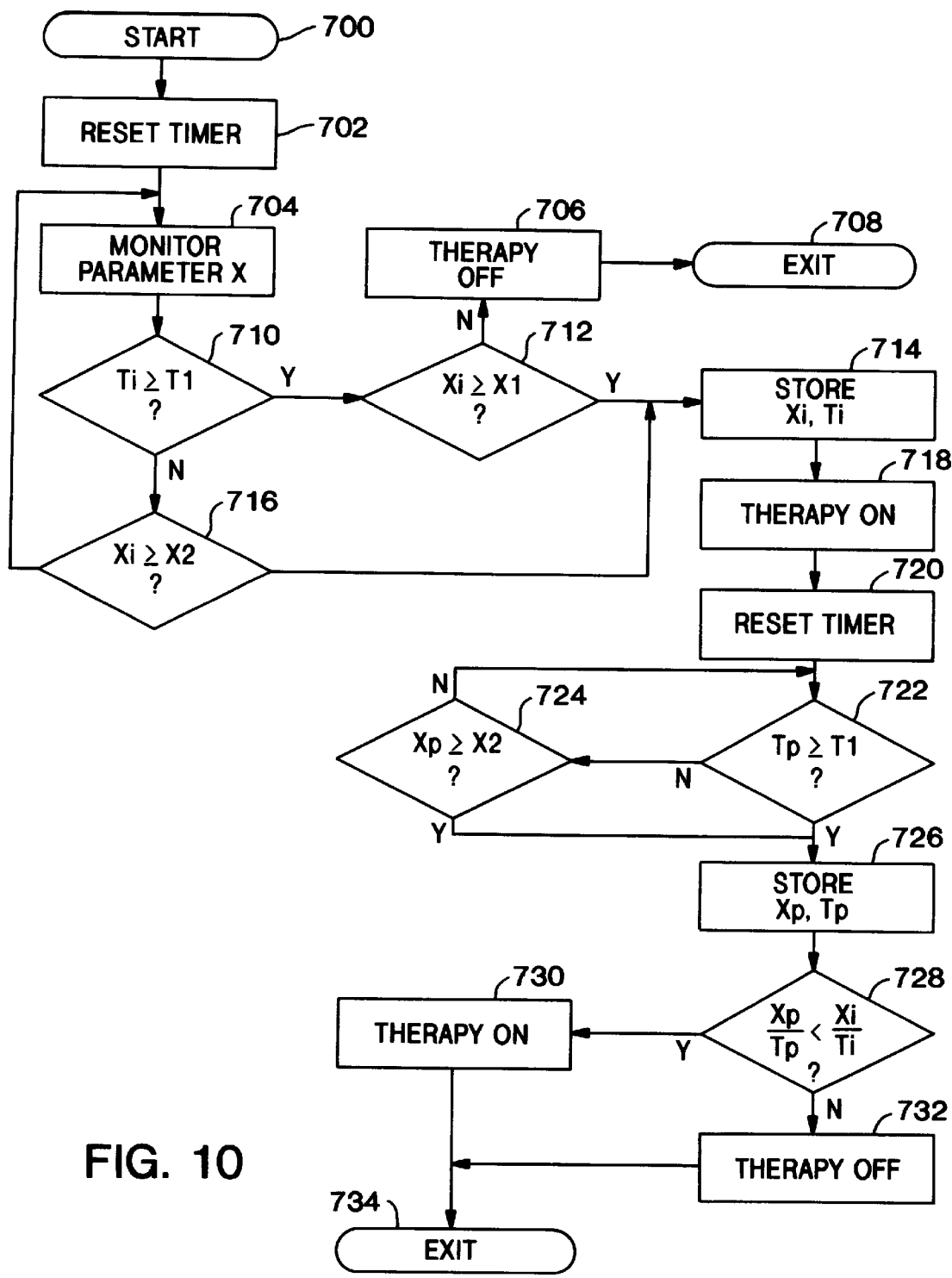
FIG. 10 is a functional flowchart, illustrating the basic operation of a pacemaker according to according to a third set of preferred embodiments of the invention.

FIG. 10 is a functional flow chart illustrating a third method of operation of a pacemaker according to the present invention which may correspond structurally to the devices of any of FIGS. 1–7. In this embodiment, the pacemaker is provided with a single arrhythmia prevention therapy and/or a single alternate electrode configuration, for example, multi-site pacing using a conventional bradycardia pacing mode, rate stabilization pacing at single or multiple sites as described above or any of the other arrhythmia prevention pacing modalities described in the patents cited above. In this embodiment, the device simply determines whether or not delivery of the arrhythmia prevention therapy and/or use of an alternate electrode configuration is appropriate, based upon the frequency and/or duration of occurrences of arrhythmias while the arrhythmia prevention therapy is present as compared to the frequency or duration of occurrences of arrhythmias while the arrhythmia prevention therapy is disabled.

The operation of the device according to these embodiments of the invention is initialized at 700, followed by resetting of the extended time period T I at 702. The extended time period in this case typically extends for at least a period of several days. During this time period, the device monitors a parameter "X" associated with detected tachyarrhythmias which may be, for example, cumulative duration of detected tachyarrhythmias, frequency of occurrence of tachyarrhythmias, or frequency or duration of detected tachyarrhythmias following pacing pulses as described above in conjunction with FIGS. 8 and 9. Alternatively, a combination of these parameters may be employed, as discussed below. The device continues to monitor the value of the selected tachyarrhythmia parameter until either time period T1 expires at 710 or until the value of the monitored parameter exceeds a threshold X2 at 716, indicative of a specified frequency or duration of detected tachyarrhythmias. On expiration of T I, the device checks to determine whether the value Xi of the measured tachyarrhythmia parameter exceeds a defined threshold X1 which is set to be less than X2 as described above. If not, the device determines that the incidence of tachyarrhythmias is not sufficient to justify use of the arrhythmia prevention therapy and/or alternate electrode configurations, the tachyarrhythmia prevention therapies and/or alternative electrode configurations are disabled at 706 and the device exits to normal bradyarrhythmia pacing functions at 708.

If, on the other hand, the measured value Xi of the tachyarrhythmia parameter exceeds XI during time period TI or exceeds X2, prior to the expiration of time period T I, the time (T) since initiation of the extended time period and tachyarrhythmia parameter value (Xi) are stored at 714. The arrhythmia prevention therapy and/or alternative electrode configuration is set on at 718, and the extended time period is reset at 720 to again correspond to a second extended time interval T2, which may be shorter than T1. In a fashion analogous to that described above, the microprocessor waits until either the time period T2 expires at 722 or until the measured value Xp of the tachyarrhythmia parameter exceeds a defined threshold X3, which may be less than X2, at 724, and following either event, stores the time (Tp) since resetting of the extended time period X2 and the measured value (Xp) of the arrhythmia parameter at 726. At 728, the microprocessor compares the frequency or duration of tachyarrhythmia per unit time during use of the therapy and/or alternate electrode configuration (Xp/Tp) with the frequency or duration of tachyarrhythmias in the absence of the therapy (Xi/Ti). If the frequency or duration of arrhythmias is not reduced during delivery of the arrhythmia prevention therapy and/or alternative electrode configuration, the arrhythmia prevention therapy and/or alternative electrode configuration is disabled at 732 and the device exits to normal bradycardia pacing at 734. If, on the other hand, the incidence of tachyarrhythmias is reduced during use of the arrhythmia prevention therapy and/or alternative electrode configuration, the therapy and/or alternative electrode configuration is enabled at 730 and the device exits the initialization program at 734. If multiple tachyarrhythmia parameters are monitored, they may be weighted and combined with one another and compared to a single threshold value or each monitored parameter may have its own threshold. If multiple thresholds are employed, the device may determine that the required level of arrhythmias been detected in response to one, some or all of the thresholds being met.

Figure 11:
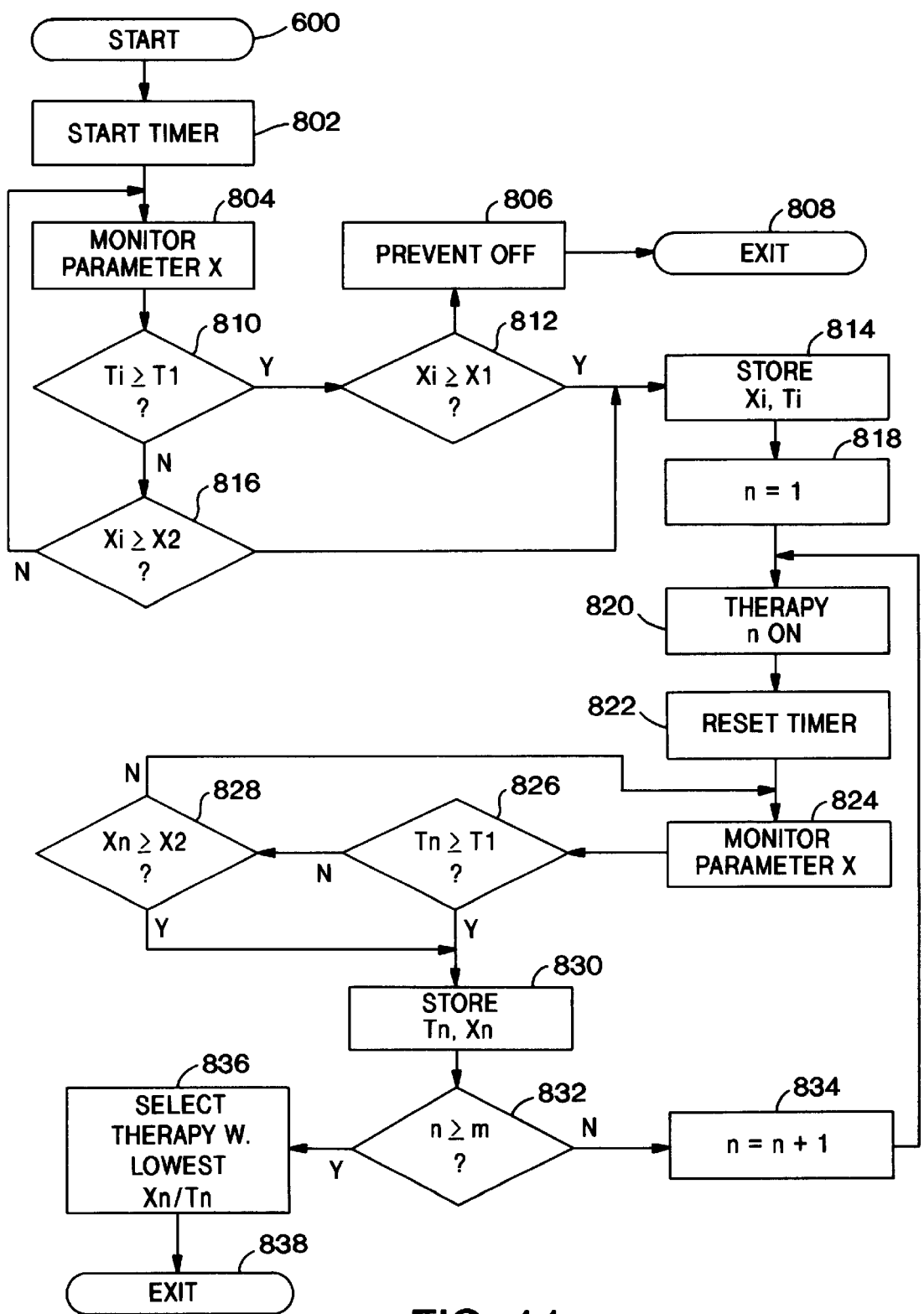
FIG. 11 is a functional flowchart, illustrating the basic operation of a pacemaker according to according to a fourth set of preferred embodiments of the invention.

FIG. 11 is a functional flowchart illustrating a more elaborate method of operation of the present invention, in which multiple arrhythmia prevention therapies and/or electrode configurations are included in a pacemaker which may correspond structurally to the devices of any of FIGS. 1–7. As described above, available operative modes may include single site arrhythmia prevention pacing therapies, multi-site pacing employing traditional bradycardia pacing modes and specialized multi-site arrhythmia prevention pacing therapies, not corresponding to convention bradycardia pacing modes. Operation of the device initially corresponds to that described to that in FIG. 10. Operation of the device according to the present embodiment is initialized at 800, with the extended time period T I initiated at 802. During TI the device monitors the parameter "X" associated with the occurrence of tachyarrhythmias, which, as described above may be frequency or duration of tachyarrhythmias, until either expiration of T1 at 810 or until the present value (Xi) of the monitored parameter exceeds a defined threshold (X2) at 816. Alternatively, a combination of these parameters may be employed, as discussed above in conjunction with FIG. 10. If on expiration of T1, the value of the monitored tachyarrhythmia parameter X, does not exceed a second threshold X1 lower than X2, the device determines that arrhythmia prevention therapies and/or alternative electrode configurations are not required at 806 and the device returns to operating at a conventional bradycardia pacemaker at 808. If the value Xi of the measured tachyarrhythmia parameter exceeds X1 on expiration of T1, or exceeds X2 prior to expiration of T1, the device stores the elapsed time (T) since the initiation of the extended time period and the value (Xi) of the measured parameter.

In this embodiment, it is envisioned that the physician has provided a prioritized list of a number "n" of tachyarrhythmia prevention therapies and/or electrode configurations, which the device will sequentially employ for the defined extended time periods to measure the relative frequency of occurrences or durations of tachyarrhythmias therein. As discussed above, these therapies and electrode configurations may differ from one another in terms of the timing of the delivery of pulses, the conditions for delivery of pulses and the locations and polarities of the electrodes according to any of the various patents cited above dealing with arrhythmia prevention therapy. The therapy and/or electrode configuration "n" to be evaluated is set equal to 1 (the first therapy and/or electrode configuration on the list) at 818, and that therapy and/or electrode configuration is enabled at 820. The timer is reset at 822 to define the extended time period T2 as described above, during which the arrhythmia parameter "X" is monitored, precisely as discussed above. On expiration of time period T2, or on the value (Xn) of the monitored parameter exceeding the higher threshold X3 at 828, the device stores the time (Tn) since initiation of the extended time period T2 and the value (Xn) of the monitored parameter associated with the currently enabled arrhythmia prevention therapy and/or electrode configuration at 830 so that these values may be employed to later select the most desirable operation of the device. The device then checks at 832 to determine whether n is greater than in, indicating that the therapy in effect is the last therapy and/or electrode configuration on the list. If not, n is incremented at 834 so that the next successive therapy and/or electrode configuration may be activated at 820.

This process continues until corresponding values for elapsed time (T) and the monitored arrhythmia parameter (Xn) have been gathered for each of the in available arrhythmia prevention therapies and/or electrode configurations. At this point, the device at 836 compares the duration or frequency of arrhythmias per unit time at 836 and selects the therapy and/or electrode configuration having the lowest frequencies of occurrence or durations of arrhythmia detected per unit time. The initialization sequence is exited at 838 and the device continues to operate in the selected tachyarrhythmia prevention mode. Following selection of an initial therapy and/or electrode configuration, the device may operate as described in conjunction with FIGS. 8 or 9 above, if desired. It should be understood in conjunction with the selection function that in the event that none of the in tachyarrhythmia prevention therapies and/or alternate electrode configurations provide a reduced frequency or duration of tachyarrhythmias per unit time, the device will disable all of the tachyarrhythmia prevention therapies and return to normal bradycardia pacing at 838.

As in the embodiment described in conjunction with FIG. 10, if multiple tachyarrhythmia parameters are monitored, they may be weighted and combined with one another and compared to a single threshold value or each monitored parameter may have its own threshold. If multiple thresholds are employed, the device may determine that the required level of arrhythmias been detected in response to one, some or all of the thresholds being met.

In the event that the operation of the device and the selection of an initial arrhythmia prevention therapy is provided as described above in conjunction with the embodiment of FIG. 11, the device may subsequently operate according to the methodology set forth in conjunction with the previously described embodiments of the invention as described in FIGS. 8 and 9, periodically changing the tachyarrhythmia prevention therapy and/or the associated set of electrodes and polarities in response to the increase in the levels of tachyarrhythmias, selecting an alternative therapy and/or set of electrodes and polarities which provide a lower incidence of tachyarrhythmias, if available. Alternatively, after either selecting a tachyarrhythmia prevention therapy or alternate electrode configuration or determining that neither is needed as described above in conjunction with the embodiments of FIGS. 10 and 11, the device may define a third extended time period, significantly longer than the first and second extended time periods. On expiration of this third time period, the device may repeat the sequence of operations described above to again determine whether tachyarrhythmia prevention therapies and/or alternate electrode configurations are desirable and if so which should be employed.

Figure 12:
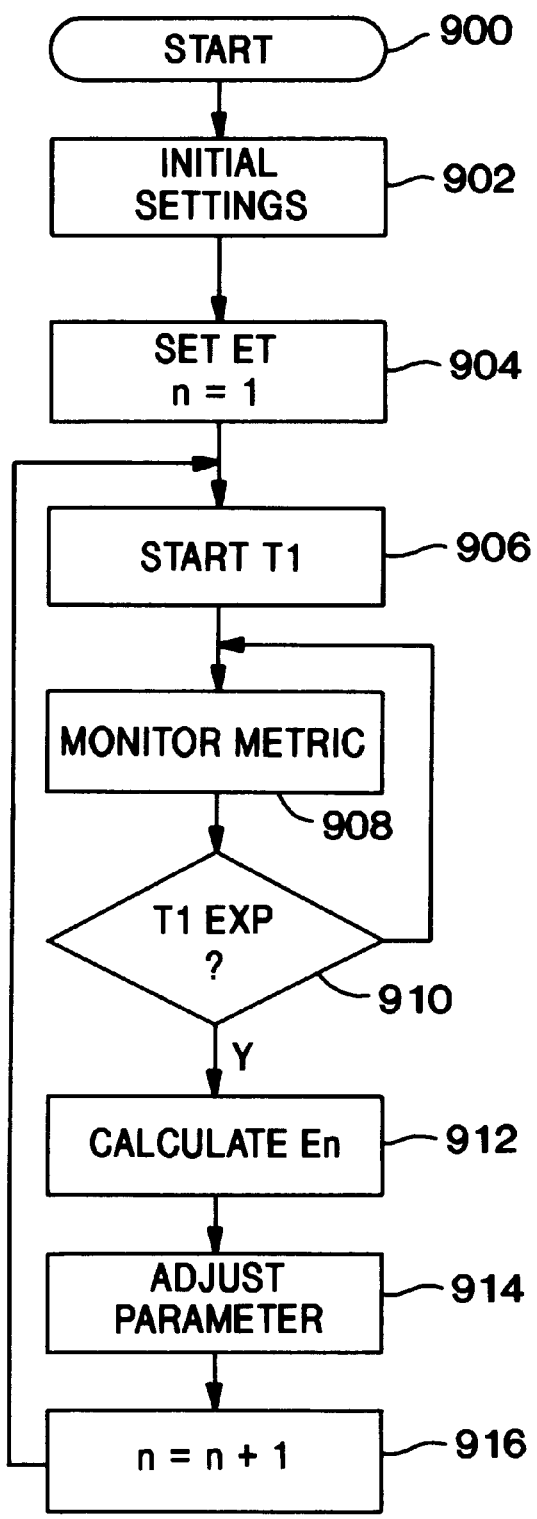
FIG. 12 is a functional flow chart illustrating the mechanism by which the present invention may optimize the parameters of a selected arrhythmia prevention pacing mode.

FIG. 12 is a functional flow chart illustrating a mechanism by which a device according to the present invention may optimize the specific parameters of a selected arrhythmia prevention pacing modality. The device may operate according to the flow chart of FIG. 12 after selecting an optimal arrhythmia prevention pacing modality according to the mechanisms described in FIGS. 1–11, discussed above. Alternatively, the device may operate according to the flow chart of FIG. 12 in conjunction with the operation of the device according to the flow charts of FIGS. 1–11 above. For example, the device may attempt to optimize a parameter or parameters of each selected arrhythmia pacing prevention modality evaluated by the device according to FIGS. 1–11, so that the evaluation of the arrhythmia prevention pacing modality may take into account the best of available settings for specific pacing modality. In such circumstance, device would preferably continue to operate according to FIG. 12, after selection of a preferred one of the available arrhythmia prevention pacing modalities.

At 900, the arrhythmia prevention pacing modality is selected, either by programming or by the mechanisms described above in conjunction with FIGS. 1–11. Initial settings of the parameters of the arrhythmia prevention pacing modality, for example, the increment to be added to preceding V-V, V-R, R-V or R-R intervals in the context of a rate stabilization algorithm as described in the above cited Mehra or Denker patents, or adjustment of a decrement to sensed P-P or A-P intervals or increment to paced A-A intervals in the context of an atrial overdrive pacing modality as described in the above Hess patent, or an adjustment to the time delay between delivery of pacing pulses at different pacing sites in the context of multi-site pacing algorithms as described above. In addition, at 904, the value of the defined endpoint range is set and the value of an optional counter "n", used in conjunction with features described below is set to 1. The defined endpoint range may be, for example, a predefined maximum number of premature atrial or ventricular events per a unit time, a range extending between defined maximum and minimum numbers of occurrences of arrhythmias such as atrial fibrillation per unit time, or the like. At 906, the device begins timing a time interval T1, during which the device will evaluate the performance of the selected antiarrhythmia pacing modality, at the initial parameter settings. During this time period, the metric to be measured, e.g., premature beats, occurrences of arrhythmias, or the like, is monitored at 908. On expiration of the interval T1 at 910, an endpoint $E_n$ corresponding to the measured metric is calculated. For example, if time interval T1 extends over several days, and the measured metric is premature beats per hour, the calculated endpoint may reflect the average occurrences of premature beats per hour over the entire duration of time interval T1 or may reflect the average rate of occurrences of premature beats per hour over the later portion of time period T1. After calculation of $E_n$, its value is compared to the defined endpoint range, and the relationship between the calculated endpoint $E_n$ and the defined endpoint range is employed to adjust the setting of one or more parameters of the arrhythmia prevention pacing modality at 914. At 916, the value "n" of the optional counter is incremented, and a new time interval T1 is initiated at 906.

Figure 13:
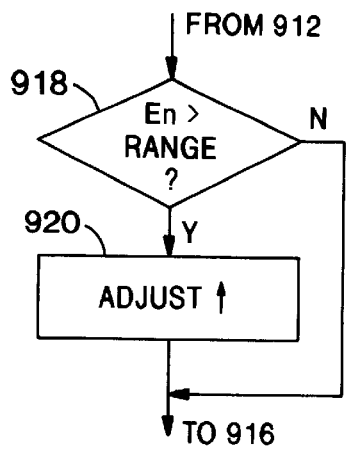
FIGS. 13, 14 and 15 represent alternative mechanisms for adjusting the parameters of an arrhythmia prevention pacing modality, in the context of the functional flow chart of FIG. 12.

FIG. 13 illustrates one of the simplest mechanisms by which a device according to the present invention may adjust the parameters of an arrhythmia prevention pacing modality. In this context, it is assumed that the desired endpoint range is defined by a value which the physician feels is the upper bound of an acceptable level of occurrences of arrhythmic events. If the measured endpoint $E_n$ is greater than the upper bound of the defined endpoint range, the parameter settings of the arrhythmia prevention pacing modality are determined to be unacceptable, and the parameters are adjusted in a defined direction in order to make the prevention pacing modality more aggressive, i.e., more likely to prevent occurrences of arrhythmia. For example, in the context of adjustment of an atrial overdrive pacing mode as in the above cited Hess et al. patent, the decrements to the measured A-P or P-P interval may be increased, in order to decrease the relative number of occurrences of spontaneous beats. In the event that the value of $E_n$ is already less than the upper bound of the defined endpoint range, the parameters of the arrhythmia prevention pacing modality are determined to be acceptable, and are not adjusted.

Figure 14:
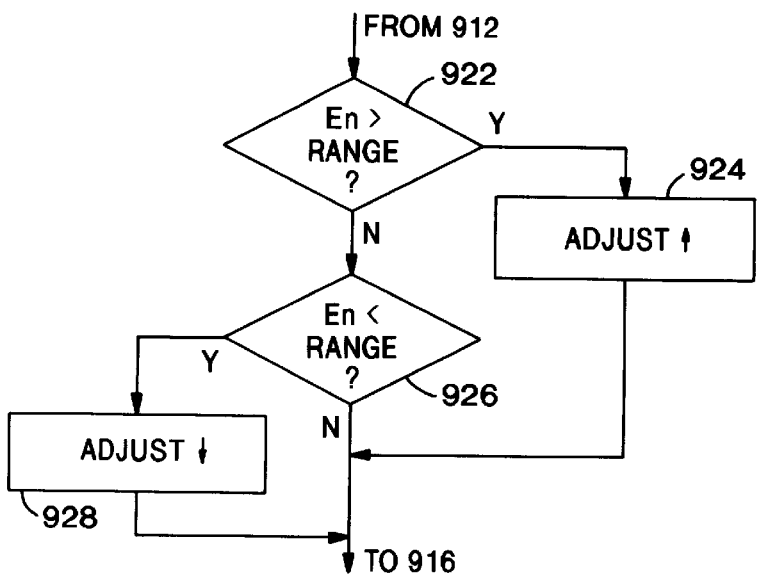

FIG. 14 illustrates a somewhat more complex mechanism for adjusting the parameters of an arrhythmia prevention pacing modality, in which the desired endpoint range has defined non-zero upper and lower bounds. At 922, the device compares $E_n$ to the upper bound of the desired endpoint range, in the fashion described in conjunction with block 918 of FIG. 13, and performs a corresponding adjustment of the arrhythmia prevention pacing parameters at 924. However, in this case, if the measured value of $E_n$ is less than the lower bound of the defined endpoint range at 926, the device adjusts the parameters of the arrhythmia prevention pacing modality in the opposite direction at 928, decreasing the aggressiveness of the therapy in order to avoid over-treating the patient.

For example, if the measured metric is occurrence of premature ventricular depolarizations, and the arrhythmia prevention pacing modality is rate stabilization pacing as described in conjunction with the above Denker and Mehra patents, a number of premature ventricular beats in excess of the desired endpoint range may trigger a decrease in the increment added to a preceding R-R, V-V, R-V or V-R interval to define the next subsequent pacing interval. The result would be an increased ability to prevent occurrences of premature ventricular depolarizations, but at the cost of an increased number of delivered pacing pulses. Conversely, in the event that the number of premature ventricular beats is less than the defined endpoint range, the value of the increment added to the preceding measured R-R, V-R, R-V or V-V interval may be increased, increasing the likelihood of spontaneous ventricular beats and decreasing the number of required delivered pacing pulses. In this fashion, the device can optimize the parameters of the arrhythmia prevention pacing modality to reflect a balance between reduction in occurrences of premature beats and the increased current drain associated with increased delivery of cardiac pacing pulses.

A similar mechanism can be employed in the context of a device which delivers pacing pulses to multiple sites within the atria or ventricles of the heart, in order to induce a more simultaneous depolarization and prevent occurrences of premature beats or arrhythmias. For example, as discussed above in conjunction with devices as pacing electrodes and sense amplifiers associated with multiple sites within the atria or associated with multiple sites within the ventricles may be provided. In such devices, delivery of a pacing pulse at one site responsive to a sensed depolarization at another site or delivery of a pacing pulse at one site in response to delivery of a pacing pulse at another site may occur after expiration of a defined relatively short escape interval, as discussed in U.S. Pat. No. 4,928,688 issued to Mower, and incorporated herein by reference in its entirety. In this case, the longer the interval separating the sensing or pacing at a first location and the subsequent delivery of a pacing pulse at a second location, the more likely it is that the pacing pulse at the second location will be inhibited. In the context of a device operating in this fashion, the device may monitor frequency of occurrences of arrhythmias, and in response to a measured endpoint $E_n$ corresponding to frequency of occurrence of arrhythmias exceeding the defined endpoint range, the duration of the escape interval between sensing or pacing at one site and subsequent delivery of a pacing pulse at a second site may be decreased, in order to provide a more aggressive anti-arrhythmia pacing modality. Conversely, if the frequency of occurrences of arrhythmias $E_n$ is less than the defined endpoint range at 926, the escape interval between a sensed or paced event at a first location and subsequent delivery of a pacing pulse at a second location may be increased, reducing the number of delivered pacing pulses.

Figure 15:
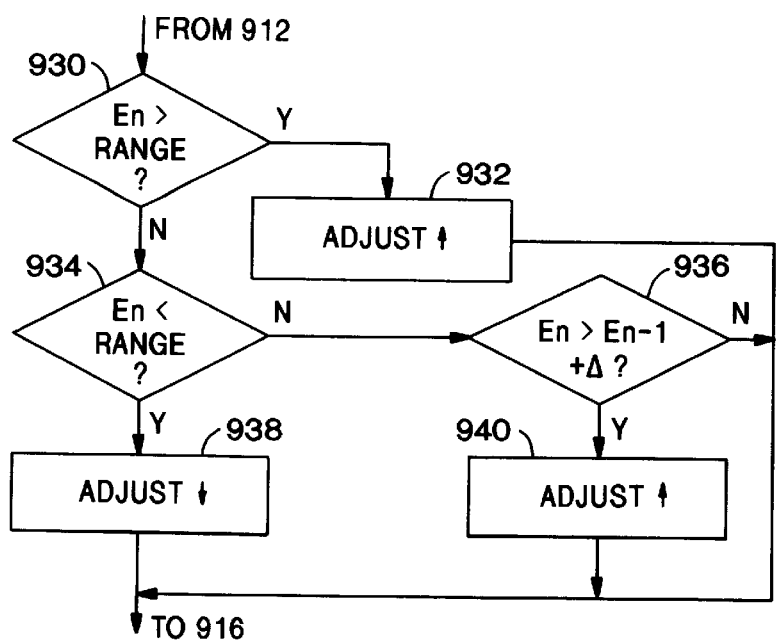

FIG. 15 illustrates a parameter adjustment methodology similar to that in FIG. 14, with the additional capability of responding to an increase in the measured metric as reflected by the most recently measured endpoint $E_n$, as compared to a previously measured endpoint $E_{n-1}$, allowing for an increase in the aggressiveness of the arrhythmia prevention pacing therapy even in the circumstance in which the resulting endpoint $E_n$ lies within the desired endpoint range. In this flow chart, functional blocks 930, 932, 934 and 936 correspond precisely to functional blocks 922, 924, 926 and 928, respectively in FIG. 14. In addition to the functionality of the mechanism illustrated in FIG. 14, responsive to a determination that the measured endpoint $E_n$ is within the defined endpoint range, the device checks at 936 to determine whether the most recently measured endpoint $E_n$ is greater than the previously measured endpoint $E_{n-1}$ plus a defined delta. If so, the aggressiveness of the arrhythmia prevention therapy is incremented at 940, in the same fashion as if the measured endpoint $E_n$ was outside the desired endpoint range at 930.

Figure 16:
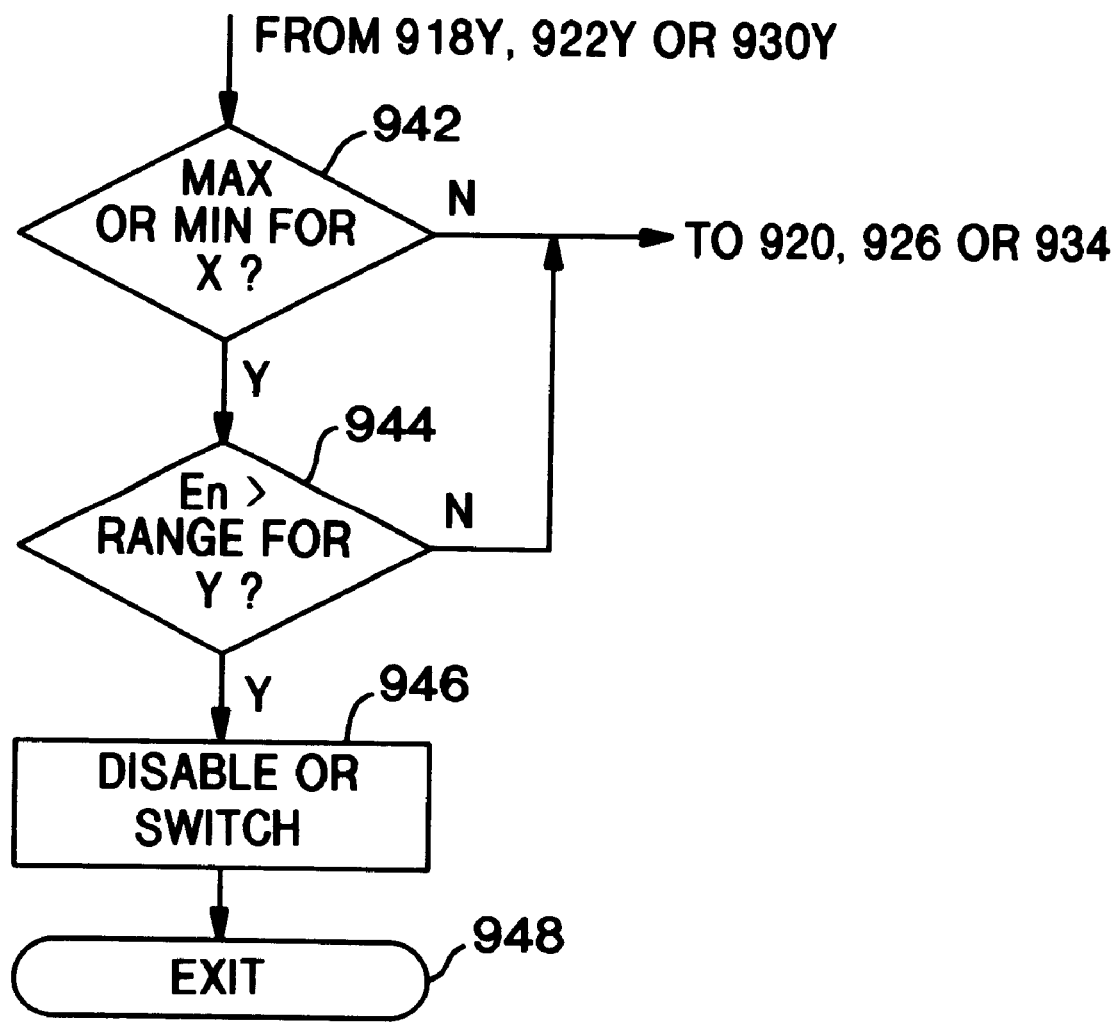
FIG. 16 is a partial functional flow chart illustrating a mechanism which may be employed in conjunction with the functional flow charts of FIGS. 12 through 15, for disabling or changing the arrhythmia prevention pacing mode presently in effect.

FIG. 16 illustrates the mechanism by which the measured metric, as reflected by the endpoint $E_n$ may be employed to terminate a arrhythmia prevention pacing modality which has proved itself to be incapable of meeting the defined level of performance required. Following a determination that the measured endpoint $E_n$ exceeds the defined endpoint range at 918, 922 or 930 (FIGS. 14, 15, 16 respectively), the device checks to see whether the adjusted parameters of the arrhythmia prevention pacing modality are at their maximum level of aggressiveness at 942, and whether they have been at the level of maximum aggressiveness for a series of "X" T1 measurement periods. If not, the device proceeds to adjust the parameters of the arrhythmia prevention pacing modality as described in conjunction with FIGS. 13–15 discussed above. If so, the device checks to determine whether the values of $E_n$ have been in excess of the defined endpoint range for a preceding series of "Y" T1 measurement periods. If not, the device continues to adjust the parameters as described in conjunction with FIGS. 13–15. In the event that the device has been operating with its arrhythmia prevention pacing parameters set at the most aggressive settings for a preceding series of measurement periods T1 and has been unsuccessful in reducing the value of the measured endpoint $E_n$ to an acceptable level for the preceding y T1 intervals, the device determines that the arrhythmia prevention pacing modality presently in effect is unlikely to be successful in achieving its desired result and disables the arrhythmia prevention pacing modality in effect at 946 or triggers a switch in alternative arrhythmia prevention pacing modality. Selection from the available pacing modalities may be made according to the descriptions in FIGS. 1–11, discussed above, and the device exits at 948 to an appropriate point within the software associated with selection between available arrhythmia prevention modes. Following selection of a new arrhythmia prevention pacing modality, the device may operate as described in the flow chart of FIG. 12, employing a newly defined desired endpoint range, newly defined initial parameters, and the like associated with the newly selected arrhythmia prevention pacing modality.

One specific embodiment of a device operating as described in conjunction with FIG. 12 et seq. may be implemented as follows. The pacemaker may be configured to operate in the atrial overdrive pacing modality described in the above-cited Hess et al. patent. In this pacing mode, the device responds to occurrences of atrial depolarizations by setting the next subsequent atrial escape interval equal to the previous A-P or P-P interval, minus a programmed decrement (–delta) and continues to pace at this escape interval until either the occurrence of a sensed atrial depolarization or delivery of a defined number (plateau step) of sequential atrial pacing pulses at the new escape interval. If a sensed atrial depolarization occurs before completion of the plateau step, a new, shortened atrial escape interval is calculated as described previously. If the plateau step is completed, the atrial escape interval is increased by a programmed increment (+delta), and the device paces at the new escape interval until either an atrial depolarization is sensed or the new plateau step is completed. This process continues, bounded by programmed upper and lower rates to provide atrial overdrive pacing at a rate which is generally only slightly above the intrinsic atrial rate.

In conjunction with the present invention, the device may operate as follows. the overdrive pacing mode is initially turned on with nominal values of +delta of 50 msec, –delta of 20 msec, and plateau steps of 10 beats. Endpoint ranges of one or more measured metrics are defined by physician programming such that one or more corresponding measured endpoints ($E_n$) must fall above the defined range to cause adjustment of the pacing mode parameters to more aggressive settings. For example, the endpoint ranges of mean PACs/day<=200 and AF episodes/day<=2 may be defined. In this embodiment, a defined mean ventricular rate range of<=85 bpm may also be defined and may be employed to trigger adjustment to a less aggressive set of pacing parameters and prevent adjustment of the pacing mode parameters to more aggressive settings. The observation period T1 may be set to 24 hours.

During the first 24 hours of data is collected with the pacing mode set at nominal values. For example, the measured endpoints ($E_n$) might be: mean PACs/day=5000 and AF/day=10, with mean V rate=72 bpm. Due to one or both of the PAC/day and AF/day values exceeding the defined acceptable ranges, the pacing parameters are adjusted to be more aggressive. For example, the following changes to the algorithm values may be: +delta=60 msec (increased by 10 msec), –delta=10 msec (decreased by 10 msec.), and plateau steps=20 beats (increased by 10 beats). Any one of these changes may be made or all of the changes may be made simultaneously for increasing aggressiveness of the pacing mode. During a newly initiated 24 hour T1 period, data is collected with the pacing parameters at the new settings. The new measured endpoints might be: mean PACs/day=100, AF/day=0, mean V rate=75 bpm. All of these values are within the defined ranges and hence the parameter values remain as set for this period.

Alternatively, assuming that the data is same as above for PACs and AF, but the V rate is 90 bpm. Then the pacing parameters may be made less aggressive, for example by decreasing the +delta value, increasing the –delta value and/or decreasing the plateau step. This process may continue until the pacing mode is programmed off by the physician. Alternatively, this process may be self terminating in the event that acceptable endpoint measurements are not obtained. For example, the device may continue attempting to optimize the pacing mode until the device has remained at the most aggressive or least aggressive settings for a defined number (1 or more) of successive T1 periods during which the device did not have endpoints within the defined ranges, after which the device itself disables the atrial overdrive pacing mode.

An additional embodiment of a device operating as described in conjunction with FIG. 12 et seq. may be implemented as follows. The pacemaker may be configured to operate in the atrial rate stabilization pacing modality referred to as atrial rate stabilization pacing, described in the above-cited Hill et al. patent. In this pacing mode, the device responds to occurrences of atrial depolarizations or delivered atrial pacing pulses by setting the next subsequent atrial escape interval equal to the previous A-A, A-P, P-A or P-P interval, plus a programmed increment (%delta), bounded by programmed upper and lower rates. %delta is calculated as a programmed percentage of the preceding measured interval between atrial events.

Operation of a device according to the invention employing atrial rate stabilization pacing as described in the above-cited Hill et al. patent may be as follows. An endpoint range of <=200 PAC's/day and an observation period T1 may be set to 3 days. The nominal %delta for atrial rate stabilization may be set to 25% of the preceding measured A-A, A-P, P-A or P-P interval. If the measured endpoint is 2000 PACs/day, then a more aggressive value for %delta=20%, 15%, etc. may be employed thereafter. If the measured endpoint was 100 PACs/day, then the parameters of the AS algorithm would not be adjusted. The device may also be configured to automatically terminate atrial rate stabilization pacing if ineffective to reduce PAC's in a manner analogous to that described above in conjunction with the atrial overdrive pacing mode.

An alternative or additional metric for controlling atrial rate stabilization pacing may be a measurement of RR variability to trigger changes in %delta. For example, if the RR variability was 30% of the mean R-R interval or of the median R-R interval over a certain observation period (T1), increases in the aggressiveness of the atrial rate stabilization pacing mode could be disabled and the %delta could be increased to a less aggressive value of 40% to minimize the amount of atrial pacing into sinus arrhythmia. This change in RR variability endpoint range may serve as a safety mechanism for the atrial rate stabilization pacing mode in the same way as the mean V rate serves to prevent excessive average ventricular rates in the atrial overdrive pacing mode, as discussed above.

While it is believed that for practical purposes, commercial implementations of devices employing the present invention will generally take the form of microprocessor controlled pacemakers as described above, the invention and its associated functions may also readily be practiced by means of a pacemaker based on full custom digital integrated circuitry as widely practiced in the pacing industry, or the form of a device fabricated of commercially available discrete components and circuits, so long as basic functions set forth above are preserved. Therefore, the disclosed embodiments should be considered exemplary, rather than limiting with regard to the claims that follow.

In conjunction with the above disclosure, we claim:

1. A method of cardiac pacing, comprising:
   pacing a patient's heart in a tachyarrhythmia prevention pacing mode for a first extended time period extending over more than one day;
   defining a desired range for a metric of success of said tachyarrhythmia prevention pacing mode;
   monitoring said metric over said first extended time period;
   in response to said monitored metric falling outside said range, adjusting parameters of said tachyarrhythmia prevention pacing mode to vary aggressiveness of said tachyarrhythmia prevention pacing mode.

2. A method according to claim 1, wherein adjusting parameters of said tachyarrhythmia prevention pacing mode to vary aggressiveness of said tachyarrhythmia prevention pacing mode comprises adjusting parameters of said tachyarrhythmia prevention pacing mode to increase aggressiveness of said tachyarrhythmia prevention pacing mode.

3. A method according to claim 1, wherein adjusting parameters of said tachyarrhythmia prevention pacing mode to vary aggressiveness of said tachyarrhythmia prevention pacing mode comprises adjusting parameters of said tachyarrhythmia prevention pacing mode to decrease aggressiveness of said tachyarrhythmia prevention pacing mode.

4. A method according to claim 1 or 2 or 3, further comprising:
   terminating operation of said tachyarrhythmia prevention pacing mode in response to said monitored metric persistently falling outside said range.

5. A method according to claim 4, wherein:
   terminating operation of said tachyarrhythmia prevention pacing mode in response to said monitored metric persistently falling outside said range comprises terminating operation of said tachyarrhythmia prevention pacing mode in response to said monitored metric persistently falling outside said range in while said tachyarrhythmia prevention pacing mode is at its most aggressive.

6. A method according to claim 4, wherein:
   terminating operation of said tachyarrhythmia prevention pacing mode in response to said monitored metric persistently falling outside said range comprises terminating operation of said tachyarrhythmia prevention pacing mode in response to said monitored metric persistently falling outside said range in while said tachyarrhythmia prevention pacing mode is at its least aggressive.

7. A cardiac pacemaker, comprising:
   means for pacing a patient's heart in a tachyarrhythmia prevention pacing mode for a first extended time period extending over more than one day;
   means for defining a desired range for a metric of success of said tachyarrhythmia prevention pacing mode;
   means for monitoring said metric over said first extended time period;
   means responsive to said monitored metric falling outside said range, for adjusting parameters of said tachyarrhythmia prevention pacing mode to vary aggressiveness of said tachyarrhythmia prevention pacing mode.

8. A pacemaker according to claim 7, wherein said means for adjusting parameters of said tachyarrhythmia prevention pacing mode to vary aggressiveness of said tachyarrhythmia prevention pacing mode comprises means for adjusting parameters of said tachyarrhythmia prevention pacing mode to increase aggressiveness of said tachyarrhythmia prevention pacing mode.

9. A pacemaker according to claim 7, wherein said means for adjusting parameters of said tachyarrhythmia prevention pacing mode to vary aggressiveness of said tachyarrhythmia prevention pacing mode comprises means for adjusting parameters of said tachyarrhythmia prevention pacing mode to decrease aggressiveness of said tachyarrhythmia prevention pacing mode.

10. A pacemaker according to claim 7 or 8 or 9, further comprising:
    means for terminating operation of said tachyarrhythmia prevention pacing mode in response to said monitored metric persistently falling outside said range.

11. A pacemaker according to claim 10, wherein:
    said means for terminating operation of said tachyarrhythmia prevention pacing mode in response to said monitored metric persistently falling outside said range comprises means for terminating operation of said tachyarrhythmia prevention pacing mode in response to said monitored metric persistently falling outside said range in while said tachyarrhythmia prevention pacing mode is at its most aggressive.

12. A pacemaker according to claim 10, wherein:
    said means for terminating operation of said tachyarrhythmia prevention pacing mode in response to said monitored metric persistently falling outside said range comprises means for terminating operation of said tachyarrhythmia prevention pacing mode in response to said monitored metric persistently falling outside said range in while said tachyarrhythmia prevention pacing mode is at its least aggressive.

13. A method of cardiac pacing, comprising:
    pacing a patient's heart in a tachyarrhythmia prevention pacing mode using a set of electrodes for a first extended time period extending over more than one day;
    defining a metric of success of said tachyarrhythmia prevention pacing mode;
    monitoring said metric over said first extended time period;
    in response to said monitored metric, adjusting said tachyarrhythmia prevention pacing mode.

14. A method according to claim 13, wherein adjusting said tachyarrhythmia prevention pacing mode comprises pacing said patient's heart with a different set of electrodes.

15. A method according to claim 13, wherein adjusting said tachyarrhythmia prevention pacing mode comprises pacing said patient's heart with a different tachyarrhythmia prevention pacing mode.

16. A method according to claim 13 or 14 or 15, further comprising:
terminating operation of said tachyarrhythmia prevention pacing mode in response to said monitored metric.

17. A cardiac pacemaker, comprising:
means for pacing a patient's heart in a tachyarrhythmia prevention pacing mode for a first extended time period extending over more than one day;
means for defining a metric of success of said tachyarrhythmia prevention pacing mode;
means for monitoring said metric over said first extended time period;
means responsive to said monitored metric, for adjusting said tachyarrhythmia prevention pacing mode.

18. A pacemaker according to claim 17, wherein said means for adjusting said tachyarrhythmia prevention pacing mode comprises means for pacing said patient's heart with a different set of electrodes.

19. A pacemaker according to claim 17, wherein said means for adjusting said tachyarrhythmia prevention pacing mode comprises means for pacing said patient's heart with a different tachyarrhythmia prevention pacing mode.

20. A pacemaker according to claim 17 wherein said means for adjusting said tachyarrhythmia prevention pacing mode comprises means for terminating operation of said tachyarrhythmia prevention pacing mode in response to said monitored metric.

21. A method of cardiac pacing, comprising:
implanting a first electrode adjacent a patient's heart;
defining a first extended time period extending over more than one day;
employing said first electrode to pace said heart in a first tachyarrhythmia prevention pacing mode for said first extended time period;
monitoring occurrences of tachyarrhythmias over said first extended time period and
in response to occurrences of tachyarrhythmias exceeding a defined level during said extended time period, ceasing pacing in said first tachyarrhythmia prevention pacing mode.

22. A method according to claim 21, further comprises implanting a second electrode adjacent the patient's heart and further comprises the step of employing said second electrode to pace the heart in a second tachyarrhythmia prevention pacing mode after ceasing pacing using said first tachyarrhythmia prevention pacing mode.

23. A method according to claim 22, wherein the step of employing said second electrode to pace the heart in a second tachyarrhythmia prevention pacing mode comprises pacing using both said first and second electrodes.

24. A method of cardiac pacing, comprising:
implanting a first electrode adjacent a patient's heart;
employing said first electrode to pace said heart in a first tachyarrhythmia prevention pacing mode for a first extended time period extending over more than one day;
monitoring occurrences of tachyarrhythmias over said first extended time period; and
in response to occurrences of tachyarrhythmias exceeding a defined level during said extended time period, ceasing pacing in said first tachyarrhythmia prevention pacing mode.

25. A method according to claim 24, further comprising the step of employing said first electrode to pace the heart in a second tachyarrhythmia prevention pacing mode after ceasing pacing using said first tachyarrhythmia prevention pacing mode.

26. A method according to claim 25, further comprises implanting a second electrode adjacent the patient's heart, wherein the step of employing said first electrode to pace the heart in a second tachyarrhythmia prevention pacing mode comprises pacing using both said first and second electrodes.

27. A cardiac pacemaker, comprising:
a first electrode implantable adjacent a patient's heart;
means for defining a first extended time period extending over one day;
means for pacing said heart in a first tachyarrhythmia prevention pacing mode for said first extended time period, using said first electrode;
means for monitoring occurrences of tachyarrhythmias over said first extended time period; and
means responsive to occurrences of tachyarrhythmias exceeding a defined level during said extended time period for ceasing pacing in said first tachyarrhythmia prevention pacing mode.

28. A pacemaker according to claim 27, farther comprising means for using said first electrode to pace the heart in a second tachyarrhythmia prevention pacing mode after ceasing pacing using said first tachyarrhythmia prevention pacing mode.

29. A pacemaker according to claim 28, further comprising a second electrode implantable adjacent the patient's heart, wherein the means for using said first electrode to pace the heart in a second tachyarrhythmia prevention pacing mode comprises means for using both said first and second electrodes.

30. A pacemaker according to claim 28, father comprising a second electrode implantable adjacent the patient's heart and further comprising means for using said second electrode to pace the heart in a second tachyarrhythmia prevention pacing mode after ceasing pacing using said first tachyarrhythmia prevention pacing mode.

31. A pacemaker according to claim 30, wherein the means for using said second electrode to pace the heart in a second tachyarrhythmia prevention pacing mode comprises means for pacing using both said first and second electrodes.

* * * * *